United States Patent
Carnés-Sánchez

(10) Patent No.: US 9,884,111 B2
(45) Date of Patent: Feb. 6, 2018

(54) PROCESS FOR PRODUCING AN ALLERGEN EXTRACT

(75) Inventor: Jerónimo Carnés-Sánchez, Barcelona (ES)

(73) Assignee: Laboratorios Leti, S.L., Tres Cantos (ES)

( * ) Notice: Subject to any disclaimer, the term of this patent is extended or adjusted under 35 U.S.C. 154(b) by 1272 days.

(21) Appl. No.: 13/577,787

(22) PCT Filed: Feb. 11, 2011

(86) PCT No.: PCT/EP2011/052049
§ 371 (c)(1),
(2), (4) Date: Sep. 20, 2012

(87) PCT Pub. No.: WO2011/098569
PCT Pub. Date: Aug. 18, 2011

(65) Prior Publication Data
US 2015/0306211 A1    Oct. 29, 2015

(30) Foreign Application Priority Data
Feb. 12, 2010 (ES) .................................. 201030199

(51) Int. Cl.
| | |
|---|---|
| A61K 39/35 | (2006.01) |
| A61K 39/36 | (2006.01) |
| A23J 1/00 | (2006.01) |
| C07K 1/00 | (2006.01) |
| C07K 14/00 | (2006.01) |
| C07K 16/00 | (2006.01) |
| C07K 17/00 | (2006.01) |
| C07K 14/37 | (2006.01) |
| C07K 14/415 | (2006.01) |
| C07K 14/435 | (2006.01) |
| C07K 14/47 | (2006.01) |
| A61K 39/00 | (2006.01) |

(52) U.S. Cl.
CPC .............. *A61K 39/35* (2013.01); *C07K 14/37* (2013.01); *C07K 14/415* (2013.01); *C07K 14/435* (2013.01); *C07K 14/43531* (2013.01); *C07K 14/47* (2013.01); *A61K 2039/577* (2013.01)

(58) Field of Classification Search
None
See application file for complete search history.

(56) References Cited

U.S. PATENT DOCUMENTS

| | | | |
|---|---|---|---|
| 4,234,569 A | 11/1980 | Marsh | |
| 4,716,120 A * | 12/1987 | Tsay | A61K 39/35 210/650 |
| 5,770,698 A | 6/1998 | Berrens | |
| 2006/0099215 A1 | 5/2006 | Buchanan et al. | |
| 2009/0162403 A1* | 6/2009 | Jacobi | A61K 39/35 424/276.1 |

FOREIGN PATENT DOCUMENTS

| | | |
|---|---|---|
| EP | 0083497 A2 | 7/1983 |
| EP | 1834648 A1 | 9/2007 |
| EP | 1834649 A1 | 9/2007 |
| GB | 1283989 | 8/1972 |
| JP | 56-045417 | 4/1981 |
| JP | S58-126816 A | 7/1983 |
| JP | H02-138130 A | 5/1990 |
| JP | H08504187 A | 5/1996 |
| WO | WO92/19970 | 11/1992 |
| WO | 94/006821 | 3/1994 |
| WO | 94/06821 A1 | 3/1994 |
| WO | WO2004/065414 A1 | 8/2004 |

OTHER PUBLICATIONS

International Search Report for PCT/EP2011/052049, ISA/EP, Rijswijk, NL, dated Apr. 6, 2011.
Katagirl "Polymerization of Japanese Cedar Pollen Antigen" Dept. of Oto-Rhino-Laryngology, vol. 90, pp. 1812-1822, 1987.
Jones et al. "Clinical efficacy and immune regulation with peanut oral immunotherapy" J Allergy Clin Immunol, vol. 124, No. 2, pp. 292-300, 2009.
Shenassa et al. "Densensitization to Peanut" J Allergy Clin Immunol, vol. 75, No. 11, Part 2, p. 177, Para 291 (Abstract).
Casanovas, M., et al., "Double-blind study of tolerability and antibody production of unmodified and chemically modified allergen vaccines of Phleum pratense", Clinical and Experimental Allergy, 2005, pp. 1377-1383, vol. 35, Blackwell Publishing Ltd.
Si-Yin Chung, et al.: Allergenic Properties of Roasted Peanut Allergens May Be Reduced by Peroxidase, Journal of Argicultral and Food Chemistry, 2004, pp. 52, 4541-4545.

* cited by examiner

*Primary Examiner* — Nora Rooney
(74) *Attorney, Agent, or Firm* — Harness, Dickey & Pierce, PLC

(57) ABSTRACT

The present invention discloses processes for producing native, depigmented and polymerized allergen extracts. The invention further discloses extracts produced via the processes, and pharmaceutical and vaccine compositions comprising the extracts, for diagnosis and treatment of allergy.

14 Claims, 7 Drawing Sheets

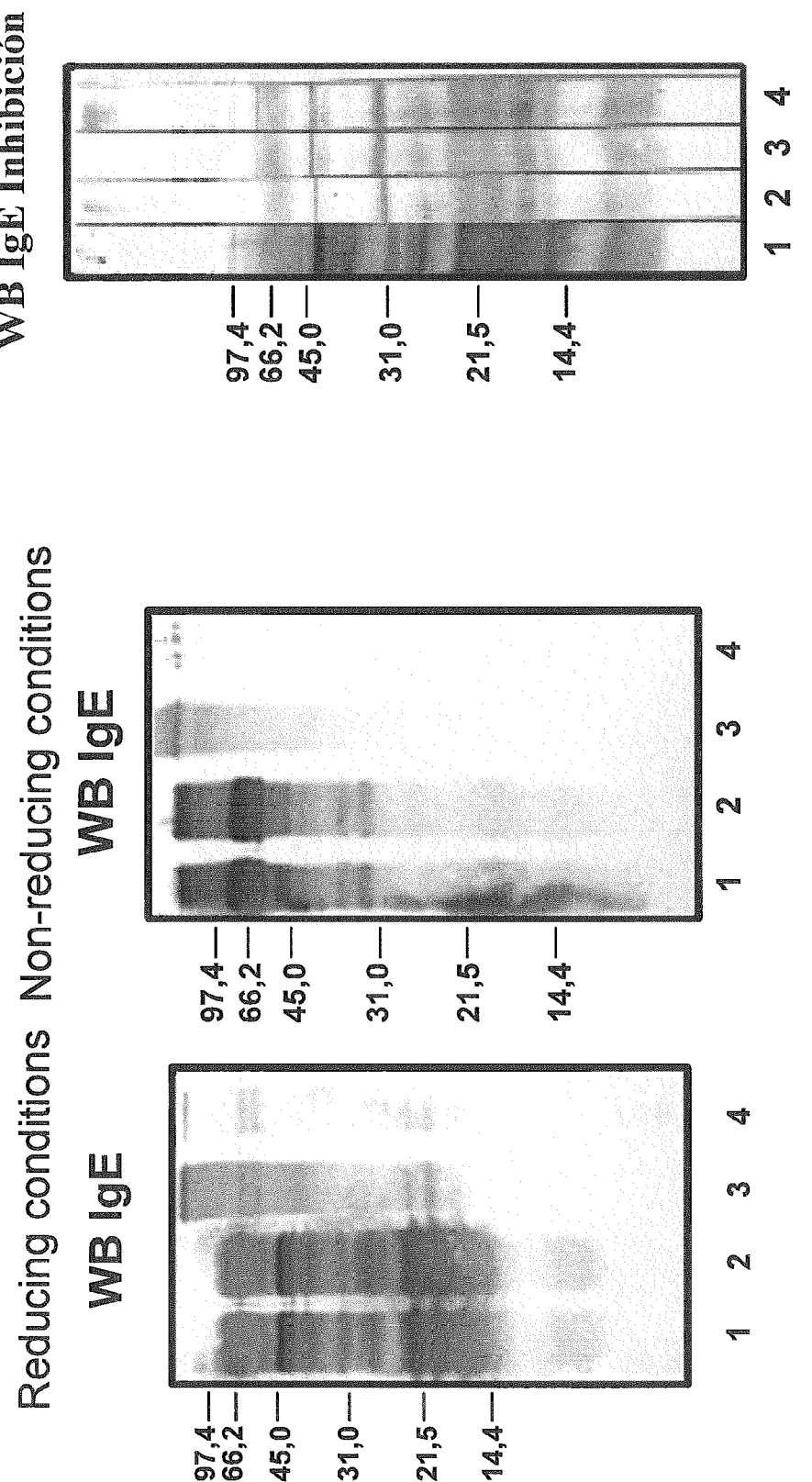

PROCESS FOR PRODUCING AN ALLERGEN EXTRACT

CROSS-REFERENCE TO RELATED APPLICATIONS

This application is a 371 U.S. National Stage of International Application No. PCT/EP2011/052049, filed Feb. 11, 2011 and published in English as WO 2011/098569 on Aug. 18, 2011. This application claims priority to Spanish Patent Application No. P201030199, filed Feb. 12, 2010. The disclosures of the above applications are incorporated herein by reference.

TECHNICAL FIELD

The invention relates to a process for producing a purified allergen extract and pharmaceutical compositions and vaccines for use in the diagnosis and treatment of allergy.

BACKGROUND TO THE INVENTION

Allergy is an acquired hypersensitivity disorder of the immune system and is triggered by exposure to harmless environmental substances known as allergens. A type I hypersensitivity reaction is characteristic of allergic reactions and results in the production of excessive amounts of IgE antibodies which in turn activate basophils and mast cells causing an inflammatory reaction. The effects may be systemic such as vasodilation, mucus secretion, nerve stimulation and smooth muscle contraction causing an anaphylaxis reaction, or confined to a particular area of the body, for example the respiratory system.

Food allergy is an emerging major public health problem that affects around 6% of school children and approximately 4% of adults and can have severe consequences, including fatal anaphylactic reactions[1]. Allergy can therefore have a significant impact on psychosocial aspects of quality of life extending beyond the immediate clinical effects of the patient's allergic condition and the daily activities of families[2]. At present the standard of care for this type of allergy includes strict avoidance of the offending allergens and treatment with epinephrine.

Peanut allergy is a Type I hypersensitivity (IgE mediated) immune response to dietary substances from peanuts causing an overreaction of the immune system. The Asthma and Allergy Foundation of America estimates that peanut allergy is the most common cause of food-related death in the USA and has estimated that it affects 0.4-0.6% of the population. Tree nuts such as pecans, pistachios, pine nuts and walnut are also common nut allergens.

To date eleven allergens (Ara h 1 through Ara h 11) have been identified from peanut (*Arachis hypogea*) and many of them have been sequenced and cloned. Based on the International Union of Immunological Societies (IUIS) nomenclature these allergens include: Ara h 1, a Cupin (Vicillin-type, 7S globulin) of 64 kDa; Ara h 2, a Conglutin (2S albumin) of 17 kDa; Ara h 3, a Cupin (Legumin-type, 11S globulin, Glycinin) of 60 kDa; Ara h 4, a Cupin (Legumin-type, 11S, Glycinin) of 37 kDa; Ara h 5, a Profilin of 15 kDa; Ara h 6, a (2S albumin) of 15 kDa; Ara h 7, a Conglutin (2S albumin) of 15 kDa; Ara h 8, a Pathogenesis-related protein, PR-10 of 17 kDa; Ara h 9, a Nonspecific lipid-transfer protein 1 of 9.8 kDa; Ara h 10, a 16 kDa oleosin, and Ara h 11, a 14 kDa oleosin.

Allergy to cats is extremely common, occurring in up to 25% of people with allergies. Cat allergy is more common than allergy to dog dander, which may be related to the potency of cat hair and dander as an allergen as well as the fact that cats are not generally bathed. Cat allergen is produced in large amounts, particularly by male non-neutered cats as the allergen is partially under hormonal control. Dander is constantly airborne, sticky, and found in public places, even where there are no cats. This is due to the dander being carried on the clothing of people who have cats, then shed in public places. Therefore, cat allergen is a component of house dust, even in homes where a cat has never lived. The size of the cat dander particles is extremely small, and is inhaled deep into the lungs. Cat dander is therefore a common cause of allergic asthma, and cat owners who are allergic to cats are more prone to the development of asthma symptoms[8, 9].

Major cat and dog allergens can be found in hair/dander extracts and saliva and are hence considered to be epithelial allergens. Eight different allergens have been identified in cat and many of them have been sequenced and cloned. Based on the IUIS website[i] these allergens include: Fel d 1 a Uteroglobin of 14 and 4 kDa; Fel d 2 a Albumin of 69 kDa; Fel d 3 a Cystatin of 11 kDa; Fel d 4, a Lipocalin of 22 kDa; Fel d 5, a Immunoglobulin A of 400 kDa; Fel d 6, a Immunoglobulin M of 800-1000 kDa; Fel d 7, a von Ebner gland protein of 17.5 kDa; Fel d 8 a Latherin-like protein of 24 kDa. The major cat allergen, Fel d 1, has been characterized extensively by protein and immunochemical techniques and was recently expressed as a recombinant allergen. Fel d 1 represents an approximately 36 kDa dimer, which is composed of two 17 kd subunits[10].

Grass allergy is one of the most common and prevalent form of allergy that affects people with histories of it during certain seasons. It is present in the air in the late spring and early summer months, which can cause allergic rhinitis, allergic conjunctivitis and asthma. Direct skin contact with grass, from sitting in the grass or mowing the lawn, can cause itching of the skin, urticaria and atopic dermatitis. One of the most representative species is *Phleum pratense*, selected as leader of the grasses group. Nine different allergens have been identified of the species *Phleum pratense*. Based on the Allergen website[i] these allergens include: Phl p 1, a Beta-expansin of 27 kDa; Phl p 2, a Grass group II/III of 10-12 kDa; Phl p 4, a protein of 55 kDa, Phl p 5 of 32 kDa, Phl p 6 of 11 kDa, Phl p 7 a calcium binding protein of 6 kDa, Phl p 11, Ole e 1-related protein of 20 kDa, Phl p 12 a profilin of 14 kDa and Phl p 13, polygalacturonase of 55 kDa.

*Phragmites* is a genus belonging to the group of grasses. Several species have been described including *P. australis*, or *P. communis*. *Phragmites communis* pollen has been reported to be allergenic in different areas. Pollination occurs between summer and fall depending on latitude and elevation.

Five different proteins with IgE binding capacity have been identified in genus *Phragmites*. Based on the Allergome website[i] these allergens include: An expansin of 30 kDa; a protein belonging to the group 4 of grasses of 60 kDa; a ribonuclease of 35 kDa, a profilun of 14 kDa and finally a polygalacturonase.

Ragweed (*Ambrosia*) are weeds that growth mainly in central Europe. A plant lives only a season but the plant produces up to thousand of pollen grains. Warmth, humidity and breeze after sunrise help to release the pollen grains. Until now three different species have been related with allergy symptoms (*Amborsia artemisiifolia* (short ragweed), *A. psilostachya* (Western ragweed), and *A. trifida* (Giant ragweed)). Ten different allergens have been identified in short ragweed and many of them have been sequenced and cloned. In the case of *Amborsia artemisiifolia*, these are termed Amb a 1 to Amb a 10 according to the international nomenclature for allergens. Based on the IUIS website[i] these allergens include: Amb a 1 a Pectate lyase of 38 kDa; Amb a 2 a Pectate lyase of 38 kDa; Amb a 3 a Plastocyanine of 11 kDa; Amb a 4, a Defensin like protein of 30 kDa; Amb a 5, of 5 kDa; Amb a 6, a lipid-transfer protein of 10 kDa; Amb a 7 a Plastocyanin of 12 kDa; Amb a 8 a Profilin of 14 kDa; Amb a 9 a Polcancin of 10 kDa and Amb a 10, a Polcalcin like protein of 18 kDa. For *A. psilostachya* only the allergen Amb p 5 has been described with unknown biological function. Only one allergen of 5 kDa has been also described in *A. trifida*.

Weeds can be divided into homologous groups according to their classified allergenic extracts. *Ambrosia* was selected as one of the leaders of this group of plants. For that reason, results obtained with this pollen extract can be extrapolated to other weeds[i].

Allergy can be treated by a number of known methods including allergen immunotherapy, specific immunotherapy (SIT), or Specific allergy vaccination (SAV) is a form of immunotherapy for allergic disorders in which the patient is vaccinated with increasingly larger doses of an allergen extract with the aim of inducing immunological tolerance. Allergen immunotherapy modulates the immune response to the allergen rather than ameliorating the symptoms induced by an allergic reaction, and can either reduce the need for medication, reduce the severity of symptoms or eliminate hypersensitivity altogether.

Although there is ample evidence that allergen immunotherapy is the only means, apart from allergen avoidance, to causally treat IgE-mediated allergic disorders caused by inhaled allergens and by stinging insects of the *Hymenoptera* group, immunotherapy with allergen extracts is not typically used for food allergy treatment. Only two recent studies have demonstrated a moderate clinical efficacy using sublingual immunotherapy in hazelnut and peach sensitized individuals respectively[3, 4].

In previous studies attempts have been made to induce a low-dose tolerance by feeding children with miniscule peanut traces which gradually become larger and larger in order to build up the immune system[4, 6]. Although early clinical trials data indicates that peanut allergy can be ameliorated using immunotherapy[7], there is currently no confirmed treatment to prevent or cure allergic reactions to peanuts, with the only effective option for atopic individuals being to avoid foods that contain or are contaminated with whole peanuts, peanut particles and peanut oils and providing ready access to self-injectable epinephrine.

One of the risks of immunotherapy is that injection of an allergen to a sensitised patient can cause a severe allergic reaction or anaphylaxis. Since its first use in the beginning of the 20$^{th}$ century, many efforts have been made to further improve the safety and efficacy of allergen immunotherapy. One approach is to employ allergen vaccines with reduced allergenicity but with maintenance of immunogenicity.

U.S. Pat. No. 5,770,698 and EP0662080 disclose a process for removal of substances and other low molecular weight material in order to purify the allergen extract and to increase the final allergen/protein content. The process consists of disrupting the electrostatic, hydrophobic or other physical forces under such conditions as to disadhere non-allergenic compounds from the allergenically active proteins. The process can consist of a mild acid treatment by lowering the pH below the pI of the respective allergen proteins.

One of the various ways of reducing allergenicity consists of chemically modifying native allergen extracts with aldehyde, mainly formaldehyde and glutaraldehyde, to produce allergoids. This aldehyde treatment leads to reaction products (mainly polymers), which have lost part of their allergenicity (i.e. exhibit a reduction of IgE reactive B-cell epitopes), reducing allergic side-effects. At the same time, the native immunogenicity of the allergen is retained owing to unchanged T-cell epitopes. This route of allergen modification has been chosen by some manufacturers of allergen vaccines to develop commercially available products based on this principle. In general, there is a trend to further purify allergen extracts, carefully selecting the most important and clinically relevant allergens.

EP1834649 and EP1834648 disclose methods for producing allergen extracts; however such methods do not sufficiently remove contaminating low molecular weight proteins.

There is a need to further improve the safety and efficacy of medicaments for use in the immunotherapy of allergic disorders by optimising the allergen purification process to ensure that contaminating low molecular weight proteins, irritants and toxic components are eliminated.

SUMMARY OF THE INVENTION

The inventors have developed an intermediate step prior to polymerisation to further improve the polymerisation process and reduce the allergenicity of certain extracts, such as mites, pollens, including grasses, weeds and trees, epithelial allergens and food allergens, prior to the treatment with glutaraldehyde.

It is an object of the present invention to provide a process for the preparation of extracts comprising allergens, and pharmaceutical compositions and vaccines for the treatment of allergy. It is a further object to provide an optimally efficacious allergen extract with reduced IgE binding capacity but which retains its immunogenic capacity.

According to a first aspect of the present invention, there is provided a process for producing an allergen extract comprising:

a) contacting a source material comprising an allergen with a liquid extraction agent to produce a mixture containing lipids dissolved in liquid phase and a solid phase consisting of source material residue comprising allergens and proteins.

b) subjecting the mixture to a first separation step to isolate the source material residue, c) contacting the source material residue with an allergen extract agent to produce a mixture of allergens dissolved in liquid phase, and a solid phase consisting of non-allergenic residue.

d) subjecting the mixture to a second separation step to isolate the allergens dissolved in liquid phase, to produce a crude allergen extract, e) subjecting the crude allergen extract to a low molecular fraction removal step to remove molecules having a molecular size of less than 3.5 kDa, and f) carrying out step e) until the allergen extract has conductivity of below 1000 µS/cm at 3-5° C. to obtain a purified native allergen extract.

A further treatment step may comprise g) acidifying the native allergen extract, removing molecules having a molecular size of less than 3.5 kDa, and neutralising the pH to produce a depigmented allergen extract.

The process may further comprise a polymerisation step, comprising h) contacting a native allergen extract or a depigmented allergen extract with an aldehyde, and i) removing molecules having a molecular size of less than 100 kDa.

According to a second aspect of the invention, there is provided an allergen extract obtainable according to the process of the first aspect of the present invention.

According to a third aspect of the invention, there is provided a purified allergen extract for use as an active therapeutic substance in the treatment of allergy.

Definitions

"Allergen" can be defined as a molecule capable of inducing an IgE response and/or a Type I allergic reaction.

The term "depigmented" referred to herein can be defined as a semi purified allergen extract obtained from a native extract by removal of irrelevant substances including the adsorbed pigments that it may contain.

DETAILED DESCRIPTION OF THE INVENTION

The allergen extracts of the invention may be derived from any source material comprising natural allergens known to illicit an IgE mediated immune reaction in an individual. Such allergens may include food allergens (e.g. peanut), air-borne allergens (e.g. pollen from grass, tree, herb and weeds, dust mites, fungi and moulds), insect allergens (e.g. cockroach, fleas, bee and wasp venom) and epithelial allergens (animal hair, animal dander, e.g. cat and dog dander).

Pollen allergens from trees, grasses and weeds derive from the taxonomic order group of Fagales (e.g. *Alnus* and *Betula*), Lamiales (e.g. *Olea* and *Plantago*), Poales (e.g. *Phleum pratense*), Asterales (e.g. *Ambrosia* and *Artemisia*), Cayophyllales (e.g. *Chenopodium* and *Salsola*), Rosales (e.g. *Parietaria*), Proteales (e.g. *Platanus*) etc. Dust mites belong to the order group of Astigmata (e.g. *Dermatophagoides* and *Euroglyphus*). Airborne allergens derived from moulds and fungi belong to the order Pleosporales (e.g. *Alternaria*), Capnodiales (e.g. *Cladosporium*) etc.

The source material according the present invention may be any allergen, including food allergens, peanuts, whole peanuts, air-borne allergens (e.g. pollen (tree pollen, weed pollen, grass pollen, cereal pollen), dust mites, fungi, moulds)), mites, grasses, tree and weed allergens, epithelial allergens (animal hair, animal dander, e.g. cat hair and dander and dog hair and dander) and insect allergens (e.g. cockroach, fleas, bee and wasp venom).

A preferred food allergen is peanuts. More preferably the peanut allergen is *Arachis hypogeal*.

Air borne allergens may be selected from/or selected from the groups of: Tree pollen (*Alnus glutinosa, Betula alba, Corylus avellana, Cupressus arizonica, Olea europea, Platanus* sp), grass pollen (*Cynodon dactylon, Dactylis glomerata, Festuca elatior, Holcus lanatus, Lolium perenne, Phleum pratense, Phragmites communis, Poa pratensis*), weed pollen (*Ambrosia elatior, Artemisia vulgaris, Chenopodium album, Parietaria judaica, Plantago lanceolata, Salsola kali*) and cereal pollen (*Avena sativa, Hordeum vulgare, Secale* cereal, *Triticum aestivum, Zea mays*), dust mites (*Acarus siro, Blomia tropicalis, Dermatophagoides farinae, Dermatophagoides microceras, Dermatophagoidespteronyssinus, Euroglyphus maynei, lepidoglyphus destructor, Tyrophagus putrescentiae*), fungi and moulds (*Alternaria* alternate, *Cladosporium herbarum, Aspergillus-fumigatus*)

Epithelial Allergens may be selected from any animal including cat hair and dander, dog hair and dander, horse hair and dander, human hair and dander, rabbit hair and dander, and feathers.

Insect Allergens may be selected from ant, flea, mites (*Acarus siro, Blomia tropicalis, Dermatophagoides farinae, Dermatophagoides microceras, Dermatophagoidespteronyssinus, Euroglyphus maynei, lepidoglyphus destructor, Tyrophagus putrescentiae*), cockroach, wasp venom and bee venom.

Preferably the source material is selected from food allergens (*Arachis hypogeal*), pollen (*Alnus glutinosa, Betula alba, Corylus avellana, Cupressus arizonica, Olea europea, Platanus* sp, *Cynodon dactylon, Dactylis glomerata, Festuca elatior, Holcus lanatus, Lolium perenne, Phleum pratense, Phragmites communis, Poa pratensis, Ambrosia elatior, Artemisia vulgaris, Chenopodium album, Parietaria judaica, Plantago lanceolata, Salsola kali, Avena sativa, Hordeum vulgare, Secale* cereal, *Triticum aestivum, Zea mays*), dust mites (*Acarus siro, Blomia tropicalis, Dermatophagoides farinae, Dermatophagoides microceras, Dermatophagoidespteronyssinus, Euroglyphus maynei, lepidoglyphus destructor, Tyrophagus putrescentiae*), fungi and moulds (*Alternaria* alternate, *Cladosporium herbarum, Aspergillusfumigatus*), epithelial allergens (cat hair and dander, dog hair and dander, horse hair and dander, human hair and dander, rabbit hair and dander, and feathers), insect allergens (ant, flea, mites, cockroach, wasp venom and bee venom).

More preferably the source material is selected from peanut (*Arachis hypogea*), pollen (*Olea europaea, Parietaria judaica, Phragmites communis* and *Phleum pratense*), mites (*Dermatophagoides pteronyssinus*), and epithelial (cat dander).

In a preferred embodiment of the invention the source material is selected from *Arachis hypogeal, Olea europaea, Parietaria judaica, Phleum pratense, Dermatophagoides pteronyssinus, Phragmites communis, Parietaria judaica* and cat dander.

In an even more preferred embodiment of the invention the source material is selected from *Arachis hypogea, Phleum pratense, Phragmites communis, Parietaria judaica* and cat dander.

In a more preferred embodiment of the invention the allergen is *Arachis hypogeal*.

When the source material is peanut, preferably the skins are removed, or the material may be crushed or powdered. The peanuts may be toasted, roasted, fried or raw.

The source material may be treated to create a maximum surface area for contact with the liquid extraction agent. The source material may be homogenised, blended, crushed, or powdered to produce a homogenous slurry for liquid extraction. The liquid extraction step is a "defatting" step to remove lipophilic compounds such as lipids and fatty acids from the source material.

The liquid extraction agent may be acetone, which may be cold. The liquid extraction step may be performed in a ratio of 1:1 (wt of source material/wt of liquid extraction agent), or any ratio where the weight of the liquid extraction agent exceeds the weight of the source material, for example 1:2, 1:3, 1:5, 1:10. The liquid extraction step is preferably performed in a ratio of 1 kg of source material to 2 L of liquid extraction agent. The liquid extraction step is preferably performed for sufficient time for the lipids in the source material to dissolve in the liquid extraction agent, which may be for over 1 minute, preferably over 5 mins, more preferably over 30 minutes, and most preferably for 1 hour or more. The liquid extraction step may be performed at between 20-25° C., but is preferably performed cold at between 2-6° C., and most preferably between 3-5° C. During the liquid extraction step, the source material is preferably stirred or agitated with the liquid extraction agent.

The first separation step may be filtration.

After the first separation step, the source material residue may be washed with the liquid extraction agent. Optionally, the source material residue may be further extracted with the liquid extraction agent, then separated. Preferably, one, two or more further liquid extraction steps are performed. The liquid extraction of the source material residue preferably is continued until the liquid extraction agent remains transparent after contacting the source material residue.

After liquid extraction, the source material residue may be dried. The source material residue may be dried at between 2-25° C., and is preferably dried at room temperature. The drying step is preferably continued for sufficient time to allow removal of the liquid extraction agent from the source material residue, which may be between 1-24 hours, 6-18 hours, 10-14 hours and preferably for around 12 hours.

Allergens may be obtained from the "defatted" source material residue by extraction with an allergen extract agent to produce a crude allergen extract comprising allergens dissolved in liquid phase and a solid phase consisting of "unwanted" non-allergenic residue. The allergen extract agent may be an aqueous solution, and preferably comprises a buffering agent. The allergen extract agent may comprise PBS and/or NaCl, for example a solution of 0.01 M PBS/ 0.15 M NaCl. The source material residue may be extracted in the allergen extract agent in any ratio where the weight of the allergen extract agent exceeds the weight of the source material residue, for example 1:2, 1:3, 1:5, 1:10, 1:20, 1:50. Preferably, the source material residue is extracted in the allergen extract agent in a ratio of 1:10 source material residue:allergen extract agent (wt/wt). The ratio of the source material residue to allergen extract agent in the extraction step may vary but should be such that the allergens in the source material residue can dissolve in the allergen extract agent. The extraction of the source material residue with the allergen extract agent is preferably performed for sufficient time for the allergens in the source material residue to dissolve in the allergen extraction agent, which may be for between 30 minutes to 12 hours, preferably between 1-6 hours, more preferably between 2-5 hours, and most preferably for around 4 hours. The allergen extraction step may be performed at between 20-25° C., but is preferably performed cold at between 2-6° C., and most preferably between 3-5° C. During the allergen extraction step, the source material residue is preferably stirred or agitated with the allergen extraction agent.

After the allergen extraction step, the allergens dissolved in liquid phase may be separated from the non-allergenic residue, to produce a crude allergen extract. The separation step is preferably centrifugation, although many techniques to separate solid from liquid are applicable, these being well known to a person skilled in the art. Preferably, the allergens dissolved in liquid phase are centrifuged at between 2-6° C., and preferably between 3-5° C., for sufficient time to sediment the non-allergenic residue as a pellet, for example between 1 minute to 1 hour, or over 1 hour. The crude allergen extract (i.e. the supernatant containing the dissolved allergens) may be stored at between 2-6° C. The non-allergenic residue pellet may be further extracted with the allergen extract agent using the same conditions as the first allergen extraction step, and preferably for a longer extraction period such as between 4-8 hours, 8-12 hours, or over 12 hours. After the second allergen extraction step, the allergens dissolved in liquid phase may be separated from the non-allergenic residue, to produce a crude allergen extract. The crude allergen extracts from the first and second allergen extraction steps are preferably pooled for further treatment.

The crude allergen extract may be filtered, for example using 0.45 μm pore size. The crude allergen extract may be subjected to a low molecular fraction removal step to remove molecules having a low molecular size such as salts and other non-allergenic compounds. The applicant has experimentally determined that the protein and allergen composition of peanut extracts is between 8 and 150 kDa, and these allergens need to be retained during molecular fraction removal steps. For example, peanut Lipid Transfer Protein (LTP)—an important allergen—is 8 kDa and which needs to retained during the low molecular fraction removal step. In step e) molecules having a molecular size of less than 8 kDa, or 7 kDa, or 6 kDa, or 5 kDa, 4 kDa or 3.5 kDa may be removed. The low molecular fraction removal step is preferably continued until the conductivity of the allergen extract at 3-5° C. is less than 900 μS/cm, or less than 800 μS/cm, or less than 700 μS/cm, or less than 600 μS/cm, or more preferably less than 500 μS/cm. The low molecular fraction removal step is preferably continued until the conductivity of the allergen extract at 3-5° C. is between 200 and 1000 μS/cm, or between 300 and 900 μS/cm, and most preferably between 400 and 800 μS/cm.

The resulting purified native allergen extract may be filtered, for example using 0.45 and/or 0.22 μm pore size.

The native allergen extract may be used in the preparation of a pharmaceutical composition or vaccine for standardisation, diagnosis, synthesis and vaccination purposes.

The process may further comprise a further treatment step, wherein non-allergenic compounds adhering to the allergen proteins are removed using means which disrupt electrostatic, hydrophobic or other physical forces being responsible for the adherence of the non-allergenic compounds to the proteins. The means for disrupting electrostatic, hydrophobic or other physical forces may be selected from the group of chemical means consisting of acid, and alkaline materials including anion and cation-exchanging materials, salts and electric currents. The acid and alkaline chemical means may be used in an amount causing the exceeding of the Iso-electric point of the proteins. The allergen extract resulting from the further treatment step is hereinafter referred to as a depigmented allergen extract.

The further treatment step may comprise
g) acidifying the native allergen extract, removing molecules having a molecular size of less than 3.5 kDa, and neutralising the pH to produce a depigmented allergen extract.

The further treatment step preferably comprises a mild acid treatment. In the mild acid treatment the pH of the allergen proteins may be reduced to less than pH 3, for example a pH-value of between 2.0 and 2.5. The pH of the allergen proteins may be between 2.0 and 6.0. The applicant has experimentally identified that the optimum pH for disadhering the non-allergenic compounds adhering to the allergen proteins is between pH 2.0 and 2.1. A pH value lower than 2.0 leads to the protein profile of the depigmented allergen extract being incomplete, and an insufficiently low pH, for example above 3.0, leads to incomplete elimination of the non-allergenic compounds in the resulting depigmented allergen extract.

The pH of the native allergen extract may be reduced using a suitable acid, for example HCl. The acidified extract may be maintained at low pH for 1-60 minutes, preferably 5-30 minutes, more preferably 10-20 minutes, and most preferably around 15 minutes. Molecules having a molecular size of less than 3.5 kDa may be removed in a low molecular fraction removal step.

After the further treatment step, the resulting depigmented extract may be collected, and the pH of the allergen extract may be neutralised using a suitable alkali, for example NaOH. The pH may be adjusted to a value where precipitation of the proteins is avoided, for example above pH 7.0, preferably between pH 7.0 and 8.0, more preferably between pH 7.0 and 7.5, and most preferably between pH 7.3 and 7.4.

The further treatment step may comprise:

g) acidifying the native allergen extract to pH 2-2.1 and maintaining the acidified extract for 5-30 minutes, followed by subjecting the extract to a low molecular fraction removal step to remove molecules having a molecular size of less than 3.5 kDa, and adjusting the pH to 7.3-7.4 to produce a depigmented allergen extract.

The further treatment step may comprise acidifying the native allergen extract to pH 2.0 to 4.0.

The means for disrupting electrostatic forces may comprise electric currents in the form of electrophoresis. The non-allergenic compounds may have a molecular weight of less than 8,000 Da, 5,000 Da and preferably less than 3,500, and may comprise flavonoids and/or their glycosides The low molecular fraction removal step may be a dialysis step, where the extract is dialysed against a dialysate such as purified water or a buffer. The low molecular fraction removal step may be performed at between 20-25° C., but is preferably performed cold at between 2-6° C., and most preferably between 3-5° C. The low molecular fraction removal step may be performed for 12-24 hours, where the solvent, or in the case of dialysis, the dialysate, is regularly changed to maintain the reaction.

The resulting depigmented allergen extract may be filtered, for example using a 0.45 µm and/or 0.22 µm pore size, and may be frozen or freeze dried for storage.

Either of the extracts produced using the process of the present invention can be further treated. The process may further comprise a polymerisation step, comprising:

h) contacting a native allergen extract or a depigmented allergen extract with an aldehyde, and i) removing molecules having a molecular size of less than 100 kDa.

The aldehyde may be any suitable aldehyde, for example glutaraldehyde or formaldehyde.

The polymerisation step may comprise:

h) contacting a native allergen extract or a depigmented allergen extract with glutaraldehyde or formaldehyde, i) subjecting the extract to a molecular fraction removal step to remove molecules having a molecular size of less than 100 kDa, and j) carrying out step i) until the allergen extract has a conductivity of below 210 µS/cm at 3-5° C. and/or is absent of glutaraldehyde to obtain a polymerised allergen extract or a depigmented polymerised allergen extract.

Where the extract for polymerisation is freeze-dried, it may be reconstituted in a buffer, for example 0.01M PBS/ 0.15M NaCl, to a final concentration of 0.1-500 mg/ml, preferably 1-100 mg/ml, and most preferably 10-50 mg/ml.

The polymerisation reaction is preferably performed to completion, such that protein bands <100 kDa (e.g. 14-25 kDa) are not detectable by non-reducing SDS-PAGE in the polymerised extract. The applicant has experimentally determined (see table 2) that two parameters influence the optimal conditions for polymerisation.

Firstly, the final concentration of glutaraldehyde is important, whereby increasing concentrations of glutaraldehyde decrease polymer yield and increase residue yield obtained by centrifugation before dialysis. In contrast to previously known polymerisation conditions employing a glutaraldehyde concentration of around 5 mg/ml (i.e. 0.009 ml glutaraldehyde per ml of allergen extract), the optimal glutaraldehyde concentration was experimentally determined to be approximately double that of the known amount, i.e. 10 mg/ml (0.02 ml glutaraldehyde per ml of allergen extract). The aldehyde may be added in a range of 1-20 mg/ml. Whilst employing previously known amounts of a final concentration of glutaraldehyde can lead to some polymerisation of the allergens, it is preferred that the aldehyde is added to a final concentration of 10 mg/ml or in a ratio of 0.02 ml glutaraldehyde per ml of extract to achieve optimal polymerisation.

Secondly, the applicant has determined that decreasing the addition rate of glutaraldehyde decreases polymer yield and increases residue yield. The aldehyde may be added to the extract at a constant speed, for example between 0.001-0.5 ml per minute (1-500 µl/min, 60-3000 µl/hour).

The polymerisation reaction may be maintained for between 1-12 h, preferably 7 hours at room temperature. The polymerisation reaction may be stopped using glycine in a proportion of 40 mg per ml of polymerised extract solution. The stopped reaction may be maintained overnight at 3-5° C., preferably under stirring. The polymerised allergens in liquid phase may be separated from insoluble residue to produce a polymerised allergen extract or a depigmented polymerised allergen extract. The separation step is preferably centrifugation, although many separation techniques are applicable, these being well known to a person skilled in the art. Preferably, the extract is centrifuged at between 2-6° C., and preferably between 3-5° C., for sufficient time to sediment the insoluble residue as a pellet, for example between 1 minute to 1 hour, or over 1 hour. The supernatant (containing the soluble allergens) may be collected and subjected to molecular fraction removal step (i).

In step i) molecules having a molecular size of less than 150 kDa may be removed. Molecules with a molecular weight over 3 MDa have been found to precipitate and may also be removed during the polymerisation step.

Preferably the molecular fraction removal step is a dialysis step, where the extract is dialysed against a dialysate such as purified water or a buffer, at 3-5° C. The molecular fraction removal step may be continued until the conductivity measured at 3-5° C. is less than 200 µS/cm, more preferably less than 175 µS/cm, more preferably less than 150 µS/cm, more preferably less than 125 µS/cm, more preferably less than 100 µS/cm, more preferably between 50 and 200 µS/cm, and most preferably between 100 and 150 µS/cm.

The resulting allergen extract may be filtered, for example using 0.45 µm and/or 0.22 µm pore size, and may be frozen or freeze dried for storage.

Any of low molecular fraction removal steps c), e), or g) may comprise an ultrafiltration step, a diafiltration step, a dialysis step, or filtration.

In its simplest form the process of the present invention may comprise preparing a native soluble allergen extract, optionally further treating the extract, for example via mild acid treatment, to remove non-allergenic compounds having a low molecular size, and polymerising the extract using an aldehyde. The native soluble allergen extract may be peanut, pollen, grass, epithelial, mould, fungi, insect or mite allergens. The process of the present invention yields an allergen extract which exhibits reduced IgE binding capacity but which retains its immunogenic capacity.

The present invention further comprises a treatment for allergy and a diagnostic drug for allergy, both comprising allergen extracts produced by the processes of the present invention, as the active ingredient. The allergy may be associated with exposure to various allergens which illicit an IgE mediated allergic response as discussed herein.

According to a second aspect of the present invention there is provided an allergen extract obtainable according to the process of the first aspect of the present invention. There is provided a purified allergen extract for use as an active therapeutic substance. There is provided a native allergen extract, a polymerised native allergen extract, a depigmented allergen extract, a depigmented a polymerised allergen extract obtainable according to the process of the first aspect of the present invention. Preferably, the extract is a polymerised native allergen extract, and more preferably a depigmented polymerised allergen extract.

The allergen extract may be selected from peanut (*Arachis hypogeal*), pollen (*Olea europaea, Parietaria judaica, Phragmites communis, Parietaria judaica* and *Phleum pratense*), mites (*Dermatophagoides pteronyssinus*), and epithelial (cat dander).

The allergen extract may be for use in the treatment of allergy. In a preferred embodiment the allergen extract *Arachis hypogeal* may be for use in the treatment of peanut allergy.

The depigmented polymerised allergen extract may be characterised by the following physicochemical and biological properties:
 i. Soluble in water,
 ii. Absence of non-polymerised allergens/proteins with a molecular weight lower than 100 kDa (identified as bands by SDS-PAGE in non-reducing conditions)
 iii. Absence of IgE recognition bands with a molecular weight lower than 100 kDa (identified by immunoblot in non-reducing conditions)
 iv. Absence of polymerised molecules with a molecular weight lower than 100 kDa (determined by size-exclusion chromatography with HPLC).
 v. 75% reduction of the free amino groups with respect to the native extract (determined by the fluram method).
 vi. Reduction of the biological potency (95%) with respect to the native allergen extract (determined by IgE ELISA inhibition experiments using a specific pool of sera from sensitized individuals) and
 vii. Absence of abnormal toxicity in mice.

The allergen extracts of the present invention may be for use as an active component of a medicament for the treatment of an allergic individual, with the aim of inducing tolerance to certain allergens.

There is provided the use of an allergen extract according to the present invention in diagnostics for immunological disorders, preferably to detect allergic disease. There is provided the use of a allergen extract according to the present invention for the treatment of allergy or in the manufacture of a medicament for the treatment of allergy. The use may be for immunotherapy. The use may be for standardisation, diagnosis, synthesis and vaccination purposes. The use may be in therapeutic treatment of patients, preferably in immunotherapy. The use may be in monitoring the patients during immunotherapy.

According to a further aspect of the present invention there is provided a pharmaceutical composition comprising an allergen extract according to the present invention. There is provided a pharmaceutical composition for the treatment of allergy which comprises as the active ingredient a pharmaceutically effective amount of an allergen extract according to the present invention and at least one pharmaceutically acceptable carrier or diluent. There is provided a diagnostic composition for allergy which comprises as the active ingredient a diagnostically effective amount of an allergen extract according to the present invention.

According to a further aspect of the present invention there is provided a vaccine comprising an allergen extract according to the present invention. The pharmaceutical composition and vaccine may further comprise one or more adjuvants, diluents, preservatives or mixtures thereof. The pharmaceutical composition or vaccine may comprise a physiologically acceptable carrier. As used herein, the phrase "pharmaceutically acceptable" preferably means approved by a regulatory agency of a government, or listed in the European or US. Pharmacopeia or another generally recognized pharmacopeia for use in humans.

Such pharmaceutically acceptable carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include mannitol, human serum albumin (HSA), starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like.

According to a further aspect of the present invention there is provided a process for producing an allergen vaccine comprising formulating an allergen extract according to the present invention with one or more adjuvants, diluents, preservatives or mixtures thereof.

There is provided a vaccine obtainable according to the process of the further aspect of the present invention. The vaccine may be for sub-cutaneous or sub-lingual use.

There is provided the use of a vaccine according to the present invention in the treatment of allergy, or in the manufacture of a medicament for the treatment of allergy.

According to a further aspect of the present invention there is provided a method of preventing an allergen sensitisation comprising the step of: exposing an individual to an effective amount of an allergen extract, the pharmaceutical composition or the vaccine of the present invention.

According to a further aspect of the present invention there is provided a method of treating an allergy in a sensitised individual, comprising administering to the individual an effective amount of an allergen extract, the pharmaceutical composition or the vaccine of the present invention. The allergen extract, the pharmaceutical composition or the vaccine may be administered sub-cutaneously, or sub-lingually, and may be administered as an increasing or constant dosage.

The individual may be a human or an animal, preferably a human.

BRIEF DESCRIPTION OF DRAWINGS

FIG. 7: Immunoblot analysis of 40 µg peanut allergen extracts under reducing conditions (FIG. 7a) and non-reducing conditions (FIG. 7b) using a pool of sera of peanut-allergic donors (dil. 1/20) and α-IgE-PO (120705, dil. 1/500), where in each Figure: Peanut 230209/LN native (lane 1), Peanut 230209/LD Depigmented (lane 2), Peanut 030309/LP Depigmented/Polymerised (lane 3), Peanut 030309/LP Depigmented/Polymerised residue (lane 4);

FIG. 8: Immunoblot inhibition analysis of peanut allergen extracts under reducing conditions using a pool of sera of peanut-allergic donors (dil. 1/20) and α-IgE-PO (120705, dil. 1/500), where lane 1 is a control (sera only) and lanes 2-4 use the pooled sera together with 800 µg depigmented/polymerised peanut allergen extract, 400 µg extract (lane 3), and 200 µg extract (lane 4);

The present invention is illustrated by the following examples which detail processes for the preparation, purification, further treatment and polymerisation of extracts comprising allergens.

Methods A-D detail the processes used to make the allergen extracts and Examples 1-8 describe the experimental characterisation of a depigmented polymerised or depigmented allergen extracts.

Methods

A. Defatting Process of Raw Allergen Material

Defatted extract was obtained by various methods depending on the nature of the raw material. The methods for each allergen are defined in each example.

In general, homogenised material is defatted in acetone at 3-5° C., and filtered. This step is repeated until the acetone is transparent. The defatted material is recovered and dried at room temperature until all the acetone has been removed.

B. Preparation of Native Allergen Extract.

Dried defatted material was weighed and extracted in 0.01 M PBS/0.15M NaCl in a proportion 1:10 for 4 hours at 3-5° C. under magnetic stirring. Afterwards, the solution was centrifuged for 30 minutes at 4° C. at 10.000 r.p.m. The resulting supernatant was collected and stored at 3-5° C. and the pellet was reconstituted in 0.01 M/NaCl 0.15M (1:10) and extracted overnight at 3-5° C. under magnetic stirring. The solution was centrifuged for 30 minutes at 3-5° C. at 10.000 r.p.m and the supernatant was collected and mixed with the previously obtained fraction. The combined extract was filtered using 0.45 μm pore size and extensively dialyzed in 3 kDa cut-off dialysis membranes until the conductivity was lower than 1000 μS/cm. The extract was then sterile filtered using 0.22 μm pore size.

C. Preparation of Depigmented Allergen Extract

Native extract in aqueous solution and maintained at 3-5° C. was further treated using the following procedure. Under magnetic stirring, the pH of the solution was adjusted to 2-2.1 by addition of 0.1M HCl and maintained under these conditions for 15 minutes. Afterwards the extract was dialyzed in 3.5 kDa cut-off dialysis membranes with purified water for 17 hours against 10 volumes of purified water at 3-5° C. Purified water was substituted 4 times during this period. After the mild acid treatment, the extract was collected and the pH adjusted to 7.3-7.4 using 0.1M NaOH. Finally the extract was sterile filtered until 0.22 μm, frozen and freeze-dried.

D. Preparation of Polymerised Depigmented Allergen Extract

The freeze-dried depigmented extract was reconstituted in 0.01 M PBS/0.15M NaCl to a final concentration of 15 mg/ml under magnetic stirring until completely diluted. The polymerization process consisted of the addition of glutaraldehyde using 0.02 ml of glutaraldehyde per ml of depigmented extract. The glutaraldehyde was added to the depigmented extract at a constant speed (36 ml/hour) using an automatic injector. The polymerization reaction was maintained for 7 hours at room temperature. The reaction was stopped with the addition of glycine in a proportion of 40 mg of glycerine per ml of solution. The reaction was maintained overnight at 3-5° C. under continuous magnetic stirring. Afterwards, the solution was centrifuged at 10.000 r.p.m. for 30 minutes at 3-5° C. The pellet was removed and the supernatant collected and extensively dialyzed in 100 kDa cut-off dialysis membranes with purified water (16.67 ml of water per ml of extract) in refrigerated conditions. The process was deemed finished when the conductivity was lower than 210 μS/cm and the absence of glutaraldehyde was confirmed by UV/visible scanning. Finally the extract was sterile filtered using 0.22 μm pore size, frozen and freeze-dried.

The final product consists of a freeze-dried depigmented and polymerised extract which is stored at 4° C. in freeze-dried conditions.

Immunological Characterisation

Protein Content

The protein content of native, depigmented, depigmented/polymerised extracts and the depigmented/polymerised residue was measured by the Lowry Biuret method following the manufacturer's instructions.

The results for one experimental lot for Example 1 are shown in Table 1.

Size Exclusion Chromatography (HPLC)

A lyophilized sample of the extract was resuspended in highly purified water to a final concentration of 1 mg/ml and stirred for 10-15 minutes. The sample was centrifuged at 13000 r.p.m. for 10 minutes and the supernatant was transferred to a vial for automatic injection. The column used for HPLC analysis was a PL-aquagel-OH 60 8 μm (Polymer-

Figure 1:
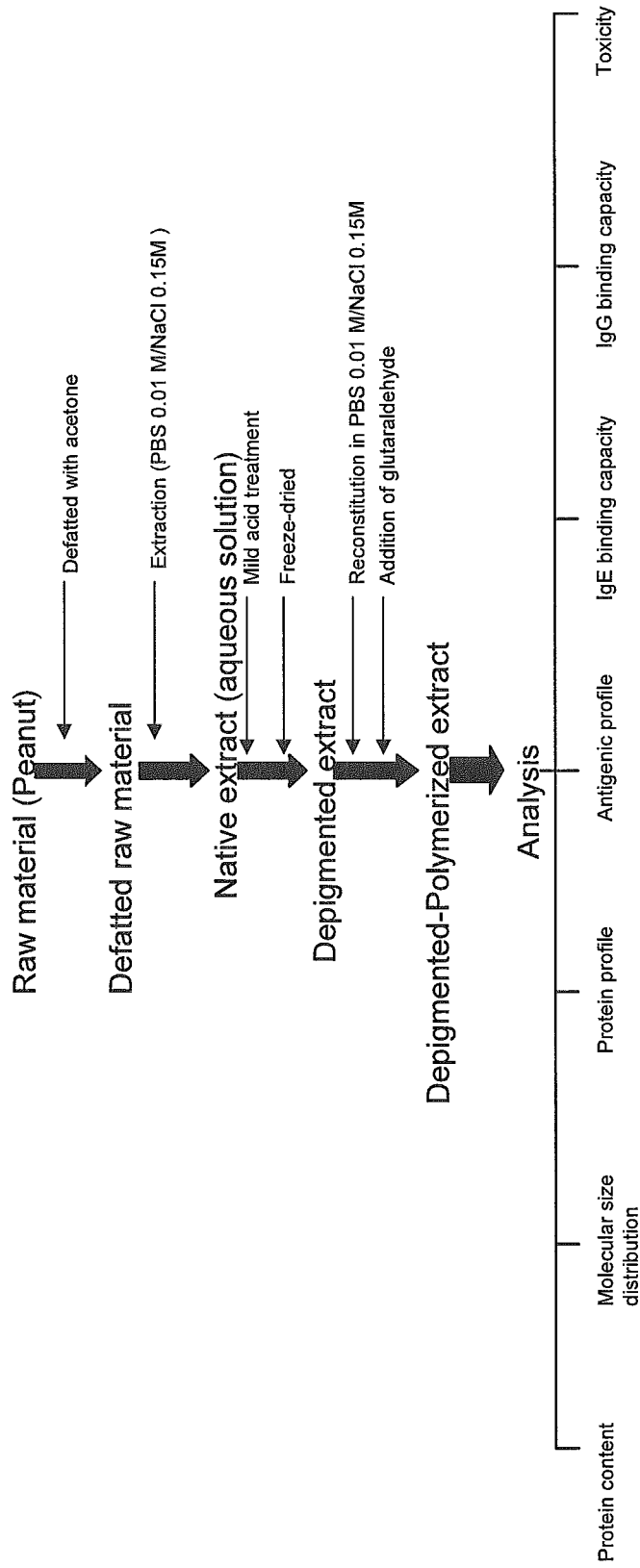
FIG. 1: Summarises the process for production of allergen extracts.
Figure 2:
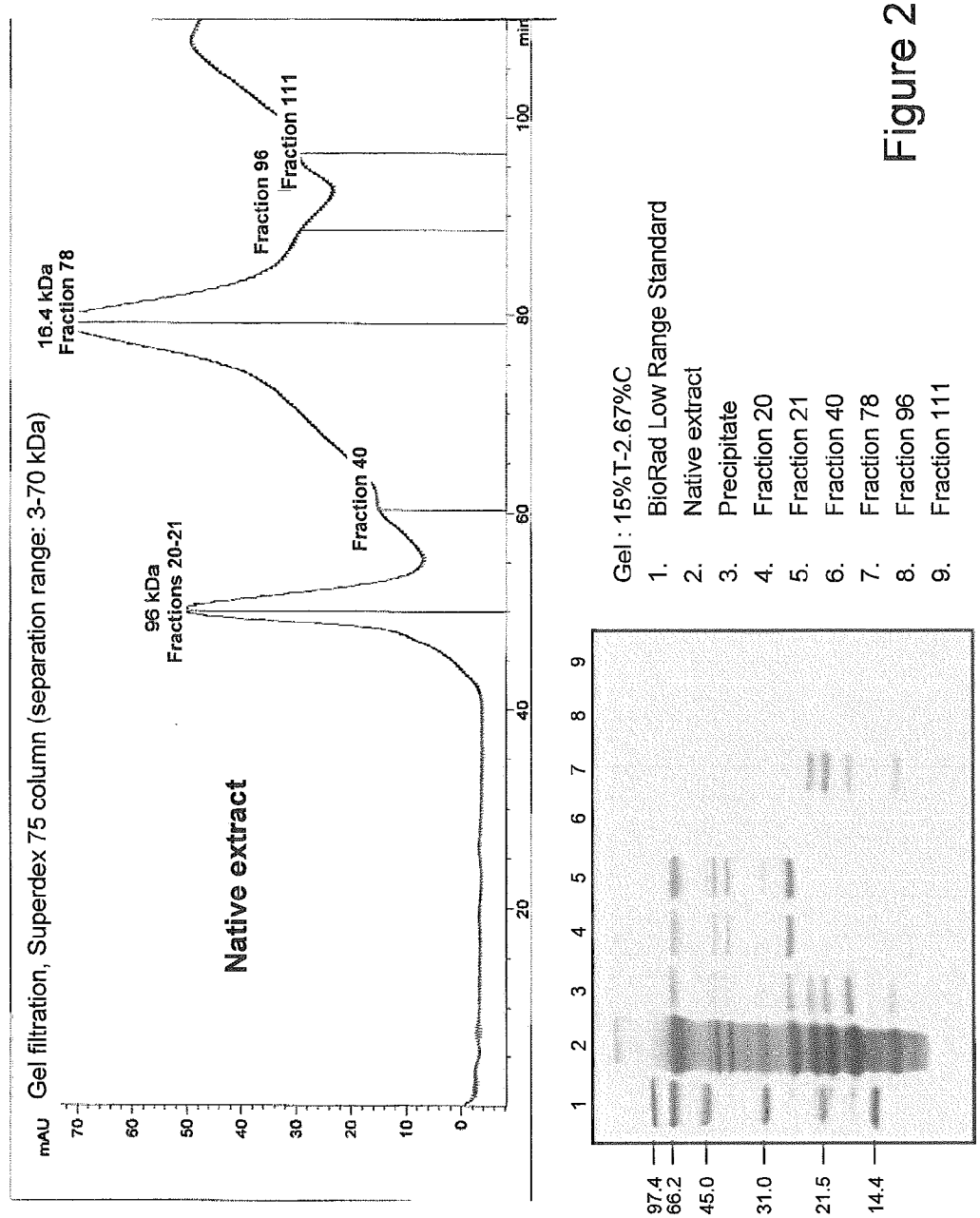
FIG. 2: HPLC analysis of native peanut allergen extract: BioRad Low Range Standard (lane 1), Native extract (lane 2), Precipitate (lane 3), Fraction 20 (lane 4), Fraction 21 (lane 5), Fraction 40 (lane 6), Fraction 78 (lane 7), Fraction 96 (lane 8), Fraction 111 (lane 9)
Figure 3:
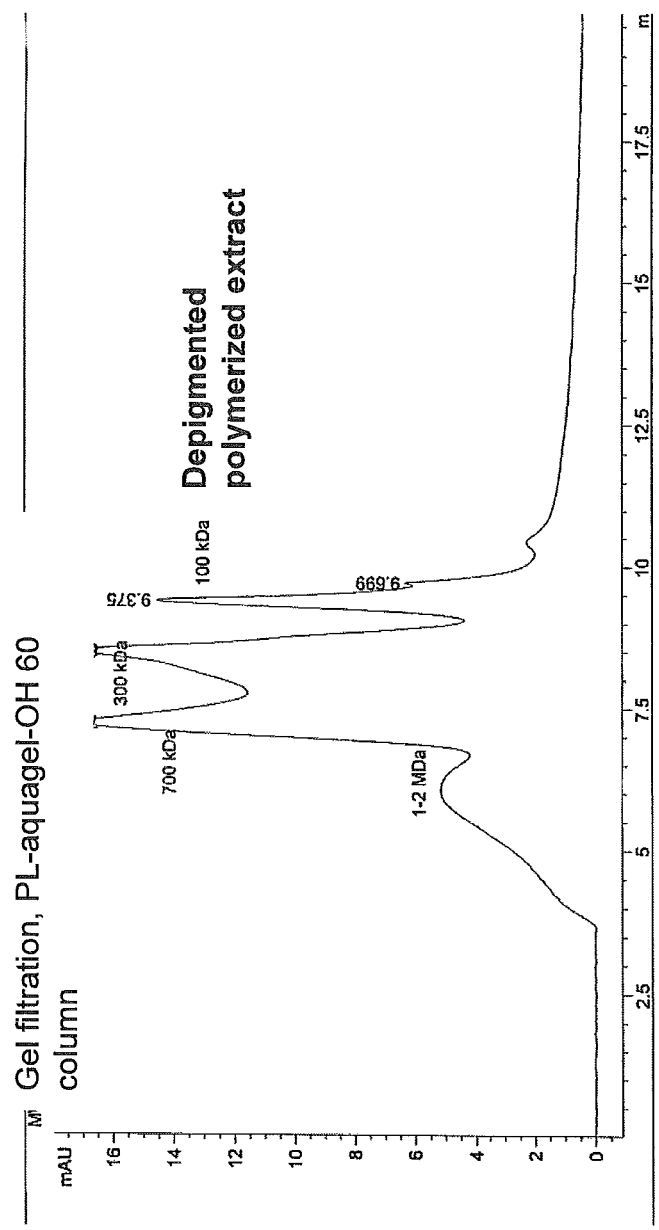
FIG. 3: HPLC analysis of depigmented polymerised peanut allergen extract.
Figure 4:
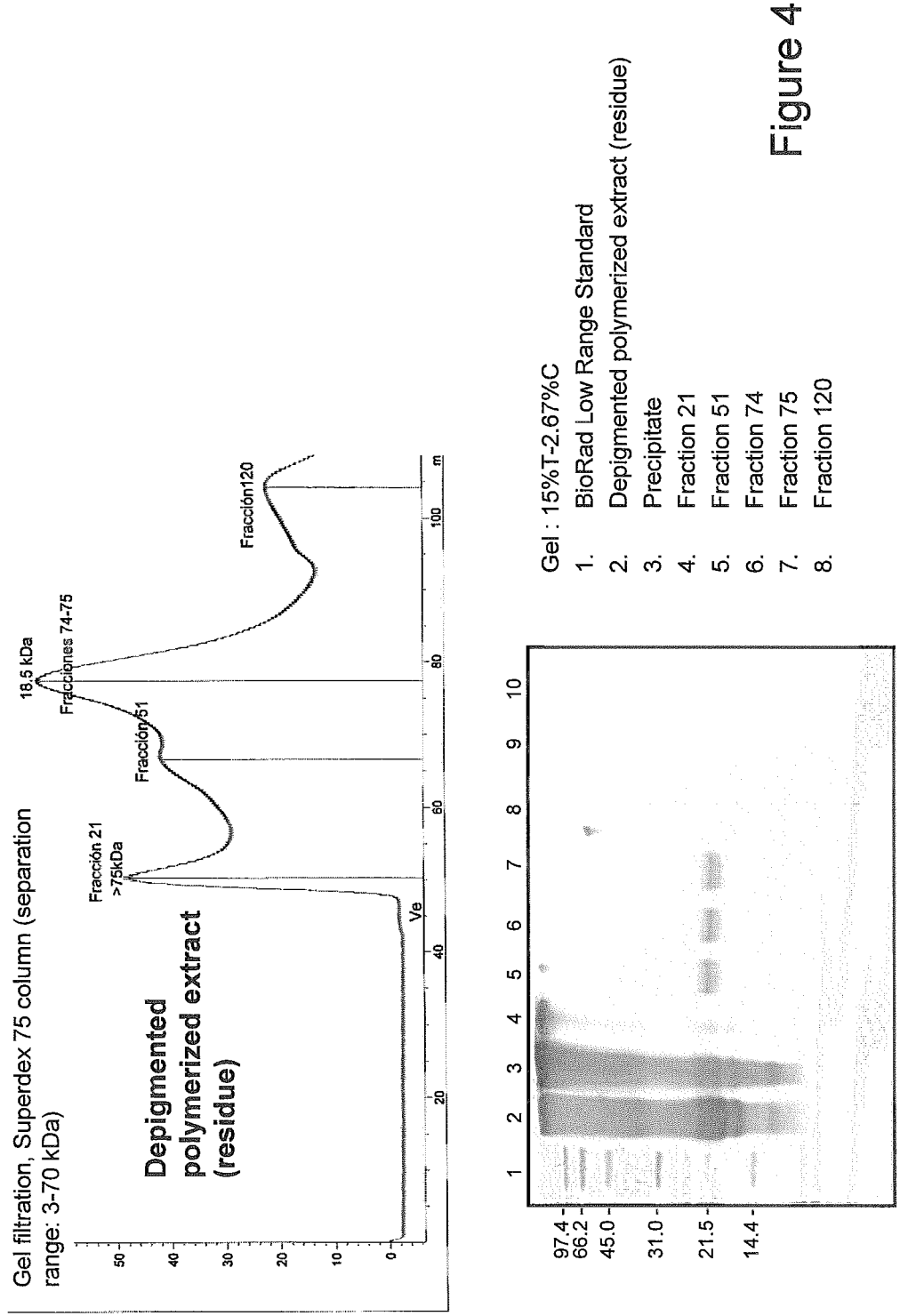
FIG. 4: HPLC analysis of depigmented polymerised peanut allergen extract residue: BioRad Low Range Standard (lane 1), Depigmented polymerized extract residue (lane 2), Precipitate (lane 3), Fraction 21 (lane 4), Fraction 51 (lane 5), Fraction 74 (lane 6), Fraction 75 (lane 7), Fraction 120 (lane 8)

Labs), previously equilibrated with water, where fractionation is based on differences in size. Samples were run with a flow rate of 1 ml/min (following manufacturer recommendations). UV signals at 254 nm and 280 nm were detected in order to obtain a chromatogram. FIGS. 2-4 show the results of the HPLC analysis.

Sodium Dodecyl Sulfate Polyacrylamide Gel Electrophoresis

Figure 5:
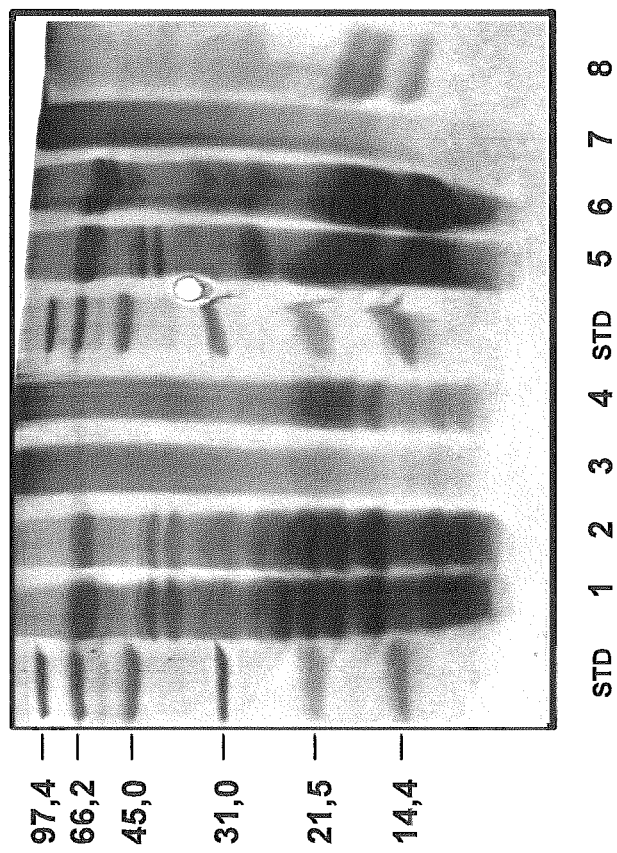
FIG. 5: SDS PAGE analysis of 40 µg peanut allergen extracts: STD (Standard Bio-Rad Low Range), Lanes 1-4 under reducing conditions, lanes 5-8 under non-reducing conditions, Peanut 230209/LN Native (lane 1), Peanut 230209/LD Depigmented (lane 2), Peanut 030309/LP Depigmented/Polymerised (lane 3), Peanut 030309/LP Depigmented/Polymerised residue (lane 4), Peanut 230209/LN Native (lane 5), Peanut 230209/LD Depigmented (lane 6), Peanut 030309/LP Depigmented/Polymerised (lane 7), and Peanut 030309/LP Depigmented/Polymerised residue (lane 8)

Sodium dodecyl sulphate polyacrylamide gel electrophoresis (SDS-PAGE) analysis was used to determine the protein/antigenic profile of the extracts. The samples were run in SDS-PAGE gels with 2.67% C, 15% T acrylamide in native or denatured conditions (buffer solution contains (3-mercaptoethanol and heated 10 minutes at 95° C.). Forty micrograms of lyophilized material of each extract was loaded onto the gels. Reference markers with known molecular weights (BioRad Laboratories, Hercules, Calif., USA) were run in the same gel. The gels were stained with Coomassie Brilliant Blue R-250 (BioRad Laboratories). The antigenic profile was studied using a scanner (Sharp JX-330; Sharp Electronics Corp, Mahwah, N.J.) and analyzed using Image Master 1-D Elite v 4.00 (Pharmacia Biotech, Uppsala, Sweden). FIG. 5 shows a Coomassie Blue stained gel, where the depigmented/polymerised allergen extract, under non-reducing conditions (lane 7) shows the absence of non-polymerised allergens/proteins with a molecular weight lower than 100 kDa.

Isoelectric Focusing

Figure 6:
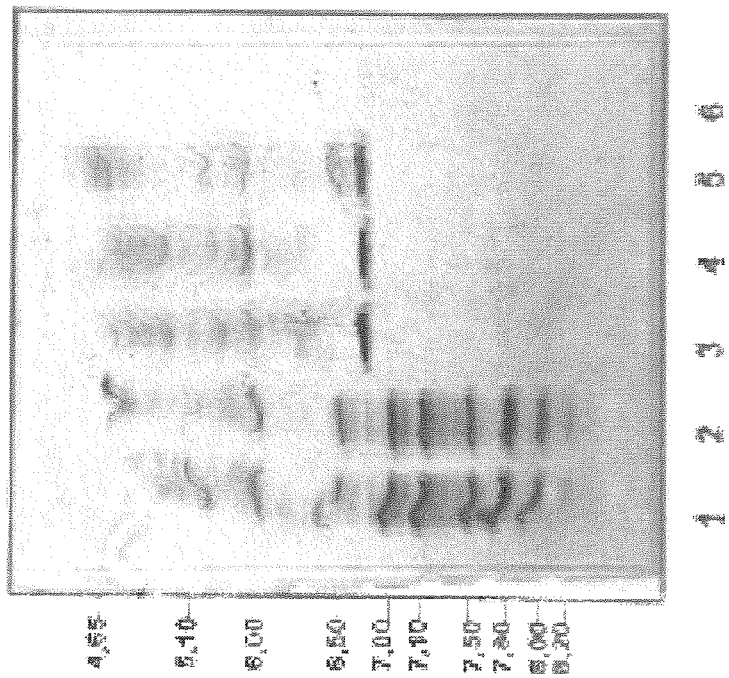
FIG. 6: IEF analysis of 40 µg peanut allergen extracts; Standard Bio-Rad IEF markers, pI 4.45-9.6 (lanes 1 and 2)), Peanut 230209/LN Native (lane 3), Peanut 230209/LD Depigmented (lane 4), Peanut 030309/LP Depigmented/Polymerised (lane 5), Peanut 030309/LP Depigmented/Polymerised residue (lane 6)

Isoelectric focusing (IEF) analysis was used to determine the protein/antigenic profile of the extracts according to the isoelectric point of the proteins. The samples were run in polyacrylamide electrophoresis gels in native conditions. Forty micrograms of lyophilized material of each extract was loaded onto the gels. Reference markers with known isoelectric points (BioRad Laboratories, Hercules, Calif., USA) were run in the same gel. Gels were stained with Coomassie Brilliant Blue R-250 (BioRad Laboratories) and the antigenic profile was studied using a scanner (Sharp JX-330; Sharp Electronics Corp, Mahwah, N.J.) and analyzed using Image Master 1-D Elite v 4.00 (Pharmacia Biotech, Uppsala, Sweden). Lanes 3-6 of FIG. 6 show the results for native (lane 3), depigmented (lane 4), depigmented/polymerised (lane 5) and depigmented/polymerised residue (lane 6).

Immunoblotting

Electrophoretic separated proteins were transferred to P-Immobilon membranes (Millipore, Bedford, Mass.). After transfer, the membranes were dried at room temperature for 4 hours. The membranes were incubated overnight with the pool of serum diluted in 0.01M phosphate-buffered saline solution Tween 2%. Specific IgE binding was detected using peroxidase-conjugated monoclonal anti-human IgE (Ingenasa, Madrid) for 2 hours. The allergenic profile was studied using the Sharp JX-330 and analyzed using Image Master 1-D Elite v 4.00. Lanes 1-4 of FIG. 7b show the results for native (lane 1), depigmented (lane 2), depigmented/polymerised (lane 3) and depigmented/polymerised residue (lane 4) under non-reducing conditions. The depigmented/polymerised allergen extract exhibits no IgE recognition bands under 100 kDa. In FIG. 8, IgE inhibition is observed using dilutions of polymerised peanut allergen extracts compared to a pooled sera of peanut-allergic donors.

IgE Inhibition

Figure 9:
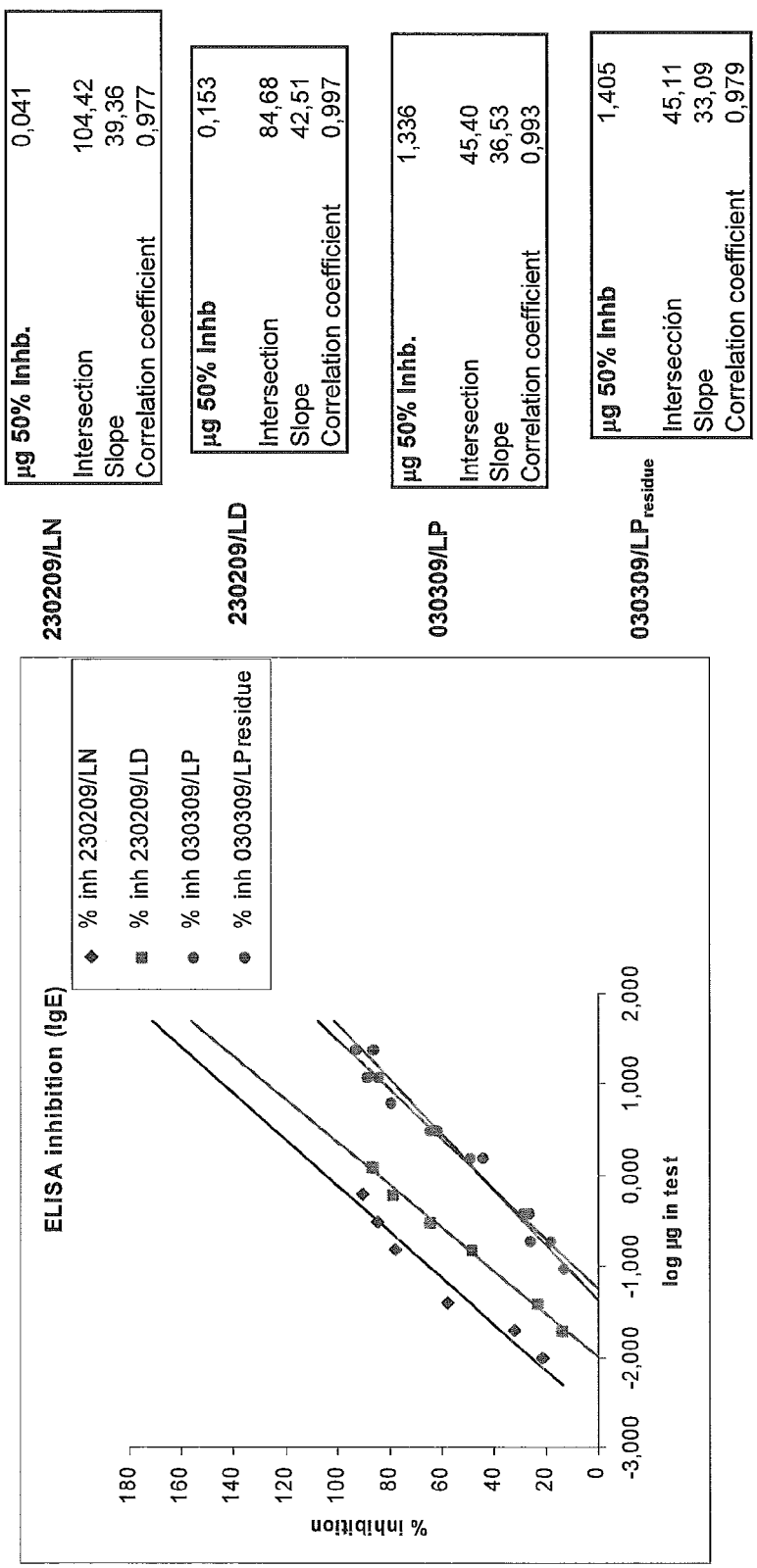
FIG. 9: ELISA based IgE inhibition analysis of peanut allergen extracts.

In vitro allergenic activity of the extracts (native, depigmented and polymerised) was tested by means of ELISA inhibition, establishing the 50% inhibition point, using a native extract as reference. Plastic microtiter plates (Immulon IV; Dynex Technologies, Chantilly, Va.) were coated with the native extract (10 µg of protein/ml) overnight. Several dilutions were made from the native, depigmented and polymerised extracts. Each dilution was incubated with a serum pool for 2 hours at room temperature. Afterward, the dilutions of the extracts were transferred to the native coated plates and incubated for 2 hours. After washing, 100 µl of anti-human IgE peroxidase was added and let to stand for 30 minutes at room temperature. After washing, the plates were developed for 30 minutes and stopped with sulfuric acid (1N). The greatest inhibition of IgE binding is observed using the depigmented/polymerised allergen extract (FIG. 9).

IgG Inhibition

In vitro allergenic activity of the extracts (native, depigmented and polymerised) was tested by means of ELISA inhibition, establishing the 50% inhibition point, using a native extract as reference. Plastic microtiter plates (Immulon II; Dynex Technologies, Chantilly, Va.) were coated with the native extract (10 µg of protein/ml) overnight. Several dilutions were made from the native, depigmented and polymerised extracts. Each dilution was incubated with a serum pool for 2 hours at room temperature. Afterward, the dilutions of the extracts were transferred to the native coated plates and incubated for 2 hours. After washing, 100 µl of anti-human IgG peroxidase was added and let to stand for 30 minutes at room temperature. After washing, the plates were developed for 30 minutes and stopped with sulfuric acid (1 N).

Fluram

The determination of free amino groups was detected in native, depigmented and depigmented-polymerized extracts. The polymerization reduces the number of free amino groups because the cross-linking between allergens is mediated by this reactive group. Native and Depigmented extracts are prepared at 25 µg/ml and depigmented-polymerized extracts at 1000 µg/ml. 6 aminocaproic acid at 2-10 mg/ml is used as standard. Evans solution is added to all the samples. Aminogroups are diluted in this buffer. Afterwards, Sodium borate buffer (0.2 M) is added to all samples and homogenized. Finally fluorescamine, previously diluted in acetone is added to the mixture and the solution measured in a fluorimeter, with excitation at 390 nm and 480 nm emission.

UV/Visible Scanning Spectrophotometry

Native, depigmented and depigmented-polymerized allergenic extracts are diluted at 1 mg/ml in PBS 0.01M. After dilution, samples are analysed at λ between 200 and 600 nm.

Biological Potency by HEP

Biological activity of the extracts (native and depigmented) are measured by REINA competition. Plastic microtiter plates are coated with anti IgE. A pool of sera from allergic individuals is added into the microplates and incubated for 30 minutes. Samples and In house reference (IHR) are previously diluted and incubated with the IHR labelled with peroxidase. Afterwards, microplates are washed and the incubated samples added to the microplates and incubated for 30 minutes. Finally, microplates are extensively washed and incubated with cromogen. Plates are read at 450 nm.

Abnormal Toxicity in Mice

Following the European Pharmacopeia recommendations, female mice (strain NMRI) were injected with 1 ml of depigmented and polymerised peanut extracts at concentrations 0.1 mg/ml and 1 mg/ml. Intraperitoneal injections were used for the administration. The observation period was 7 days after which, non significant variations in weight or behaviour were be observed in animals.

EXAMPLES

Example 1—Peanut Allergen Extract

Step A. Defatting Process of Raw Peanut Material

Peeled peanuts were homogenized in a blender to obtain a homogenized slurry. The homogenized material was defatted with cold acetone in a proportion of 1 kg slurry: 2 L acetone for 1 hour at 3-5° C. under continuous magnetic stirring to extract lipids, fatty acids, and free flavonoids. The resulting solution was filtered in a Buchner funnel. The acetone was removed and the extract was collected in a filter, and washed twice with fresh acetone. The whole process was repeated two more times until the collected acetone was transparent. After finishing the process, the defatted peanut extract was collected and dried at room temperature under a laminar flow hood for 12 hours, until the material was totally dry and all the acetone had been removed.

Depigmented polymerised peanut allergen extract was obtained in accordance with method steps B-D.

Characterisation of Peanut-Allergen Extracts

The depigmented polymerised peanut allergen extract product has to meet the following specifications:
a. Soluble product in water
b. Absence of non-polymerised allergens/proteins with a molecular weight lower than 100 kDa (identified as bands by SDS-PAGE in non-reducing conditions)
c. Absence of IgE recognition bands with a molecular weight lower than 100 kDa (identified by immunoblotting in non-reducing conditions)
d. Absence of polymerised molecules in a molecular weight lower than 100 kDa (determined by size-exclusion chromatography with HPLC)
e. Reduction of the free amino groups (75%) with respect to the native extract (determined by the fluram method)
f. Reduction of the biological potency (95%) respect to the native extract (determined by IgE ELISA inhibition experiments using a specific pool of sera from sensitized individuals)
g. Absence of abnormal toxicity in mice The pellet comprising depigmented/polymerised residue was utilised as a control in the characterisation of the native, depigmented and depigmented/polymerised extracts (refer to Table 1 and 2).

Example 2—Ragweed Allergen Extract (*Ambrosia artemisiifolia*)

Step A. Defatting Process of Raw Allergen Material

Ragweed pollen collected from the plant after pollination is defatted with cold acetone in a proportion 1:4 (w/v) under continuous stirring for 3 hours at 3-5° C. The resulting solution was filtered in a Buchner funnel and washed at least three times with fresh acetone. After finishing the process, the defatted extract was collected and dried at room temperature under a laminar flow hood for 12 hours, until the material was totally dry and all the acetone had been removed.

Depigmented polymerised ragweed (*Ambrosia artemisiifolia*) was obtained in accordance with method steps B-D. The pH of the solution is adjusted to 4-4.1 by the addition of 0.1M HCl in step 3.

The final product consists on a freeze-dried depigmented and polymerised ragweed extract, to be stored at 4° C. in freeze-dried conditions. The resulting product has to meet the following specifications:

a. Soluble product in water
b. Absence of non-polymerised allergens/proteins with a molecular weight lower than 100 kDa (identified as bands by SDS-PAGE in non-reducing conditions)
c. Absence of IgE recognition bands with a molecular weight lower than 100 kDa (identified by Immunoblot in non-reducing conditions)
d. Absence of polymerised molecules in a molecular weight lower than 100 kDa (determined by size-exclusion chromatography with HPLC)
e. Reduction of the free aminogroups (75%) respect to the native extract (determined by the fluram method)
f. Significant reduction of the biological potency respect to the native extract (determined by IgE ELISA inhibition experiments using a specific pool of sera from sensitized individuals)
g. Detection of the major allergen Amb a 1. Monoclonal antibodies
h. Absence of abnormal toxicity in mice Major Allergen Content Major allergen content Amb a 1 is measured using the Indoor Biotech kit (INDOOR Biotechnologies Inc. Charlottesville, Va., USA). Anti Amb a 1 Polyclonal IgG antibody is coated (1:1000 from the vial prepared at 1 mg/ml). Standard curve is prepared using a quantified and standard-

TABLE 1

Summary of the results obtained with one experimental lot.

| Peanut | Batch | Yield | ELISA inh. (IgE) µg 50% inh. (% potency loss) | ELISA inh. (IgG) µg 50% inh. (% potency loss) | Lowry-Biuret µg prot./mg lyoph. | Fluram µg ACA/mg lyoph. (% amino groups loss) | UV-Visible 1 mg/ml |
|---|---|---|---|---|---|---|---|
| Native | 230209/LN | 5.95% | 0.041 | 0.021 | 419.6 | 65.1 | 1.326 (264 nm) |
| Depigmented | 230209/LD | 85.3% | 0.153 | 0.144 | 372.7 | 66.9 | 1.356 (260 nm) |
| Depigmented and polymerized | 030309/LP | 9.08% | 1.336 (96.9%) | 0.699 | 348.3 | 6.45 (90%) | 2.591 (260 nm) |
| Depigmented and polymerized (residue) | 030309/LP | 46.3% | 1.405 (97.1%) | 0.627 | 234.6 | 2.82 (95.7%) | 0.192 (260 nm) | ized against the US FDA (radial immunodiffusion reference for Amb a 1, C14-RAS which contain 30 U Amb a 1/ml) ragweed extract containing an activity 2.5 U/ml of Amb a 1. Secondary antibody consists on a rabbit polyclonal IgG biotinilated antibody raise against short ragweed allergen. Native and Depigmented samples are diluted at 500 ng/ml. Major allergen content is calculated in polymerised extracts using these values.

The pellet comprising depigmented/polymerised residue was utilised as a control in the characterisation of the native, depigmented and depigmented/polymerised extracts (refer to Table 3a and 3b).

Depigmented pollen allergen extract was obtained in accordance with method step B-C The final product consists on a freeze-dried depigmented extract, to be stored at 4° C. in freeze-dried conditions. The resulting product has to meet the following specifications:
   a. Soluble product in water
   b. Similar protein profile than native extract, determined by SDS-PAGE and 2-D
   c. Similar allergenic profile than native extract, determined by immunoblot
   d. Similar protein content than native extract
   e. Similar major allergen content than native extract TABLE 3a Summary of the results obtained for Example 2 (Ragweed, *Ambrosia artemisiifolia*)

| Ragweed | Yield (%) | ELISA inh. (IgE) 50% inhibition (µg) (% potency loss) | Protein content µg prot./mg | Fluram µg ACA/mg (% reduction amino group) | UV-visible 1 mg/ml Absorbance (nm) | Amb a 1 U/mg liof. |
|---|---|---|---|---|---|---|
| Native | 12.36 | 0.022 | 201 | 62.3 | 1.102 (272 nm) | 61.3 |
| Depigmented | 77.4 | 0.011 | 288 | 82.4 | 0.766 (274 nm) | 69.2 |
| Depigmented-polymerised (0.009) | 81.7 | 0.104 | 332 | 4.04 (93.5%) | 1.665 (268 nm) | N/A |
| Depigmented-polymerised (0.013). | 72.5 | 0.120 | 359 | 4.06 (93.5%) | 1.687 (268 nm) | N/A |
| Depigmented-polymerised (0.02) | 70.13 | 0.182 | 210 | 6.3 (89.9%) | 1.610 (268 nm) | N/A |
| Depigmented-polymerised (0.018) | 68.3 | 0.141 | 274 | 3.8 (93.8%) | 1.502 (268 nm) | N/A |

TABLE 3b

Summary of the results obtained for Example 2 (Ragweed, *Ambrosia artemisiifolia*)

| Ragweed | SDS-PAGE (kDa) | Immunoblot (kDa) | Molecular size (kDa) |
|---|---|---|---|
| Native | 10-100 | 10-100 | 10-100 |
| Depigmented | 10-100 | 10-100 | 10-100 |
| Depigmented-polymerised (0.009) | >100 | Absent | >100 |
| Depigmented-polymerised (0.013). | >100 | Absent | >100 |
| Depigmented-polymerised (0.02) | >100 | Absent | >100 |
| Depigmented-polymerised (0.018) | >100 | Absent | >100 | f. Similar biological activity than native extract

TABLE 4

Summary of results obtained for Example 3 (*Olea euopaea*)

| Olea europaena | Yield (%) | ELISA inh. µ (IgE) µ 50% inh. | Protein content µg prot/mg. | UV-visible 1 mg/ml | Potency HEP-L/mg |
|---|---|---|---|---|---|
| Native | 3.64 | 0.009 | 321.6 | 1.577 (270 nm) | 257.2 |
| Depigmented pH2 | 74.0 | 0.009 | 307.4 | 1.302 (274(nm) | 196.8 |
| Depigmented pH3 | 62.0 | 0.007 | 324.2 | 1.365 (274 nm) | 204.8 |
| Depigmented pH4 | 70.7 | 0.008 | 368.7 | 1.291 (274 nm) | 221.3 |
| Depigmented pH5 | 78.2 | 0.009 | 348.8 | 1.374 (274 nm) | 257.7 |
| Depigmented pH6 | 80.2 | 0.010 | 402.1 | 1.348 (274 nm) | 247.0 |

Example 3—Pollen Allergen Extract (*Olea europaea*)

*Olea europaea* pollen collected from the tree after pollination is defatted with cold acetone in a proportion 1:4 (w/v) under continuous stirring for 3 hours at 3-5° C. The resulting solution was filtered in a Buchner funnel and washed at least three times with fresh acetone. After finishing the process, the defatted extract was collected and dried at room temperature under a laminar flow hood for 12 hours, until the material was totally dry and all the acetone had been removed.

Example 4—Pollen Allergen Extract (*Parietaria judaica*)

*Parietaria judaica* pollen collected from the plant after pollination is defatted with cold acetone in a proportion 1:4 (w/v) under continuous stirring for 3 hours at 3-5° C. The resulting solution was filtered in a Buchner funnel and washed at least three times with fresh acetone. After finishing the process, the defatted extract was collected and dried at room temperature under a laminar flow hood for 12 hours, until the material was totally dry and all the acetone had been removed.

Depigmented pollen allergen extract was obtained in accordance with method step B.

The final product consists on a freeze-dried depigmented extract, to be stored at 4° C. in freeze-dried conditions. The resulting product has to meet the following specifications:
  a. Soluble product in water
  b. Similar protein profile than native extract, determined by SDS-PAGE and 2-D
  c. Similar allergenic profile than native extract, determined by immunoblot
  d. Similar protein content than native extract
  e. Similar major allergen content than native extract
  f. Similar biological activity than native extract

TABLE 5

Summary of results obtained for Example 5 (*Parietaria judaica*)

| *Parietaria judaica* | Yield (%) | ELISA inh.(IgE) µg 50% inh. | Lowry-Biuret µg prot./mg | UV-visible 1 mg/ml | Potency HEP-L/mg |
|---|---|---|---|---|---|
| Native | 4.07 | 0.031 | 219.7 | 3.073 (266 nm) 1.492 (342 nm) | 281 |
| Depigmented pH2 | 82.7 | 0.018 | 197.9 | 2.680 (270 nm) 1,393 (342 nm) | 397 |
| Depigmented pH3 | 79.5 | 0.015 | 228.6 | 2.943 (270 nm) 1.519 (346 nm) | 430 |
| Depigmented pH4 | 83.5 | 0.017 | 213.5 | 2.769 (270 nm) 1.463 (348 nm) | 534 |
| Depigmented pH5 | 79.9 | 0.012 | 245.4 | 2.658 (272 nm) 1.504 (344 nm) | 1007 |
| Depigmented pH6 | 87.3 | 0.001 | 216.2 | 2.763 (272 nm) 1.539 (344 nm) | 954 | c. Similar allergenic profile than native extract, determined by immunoblot
  d. Similar protein content than native extract
  e. Similar major allergen content than native extract
  f. Similar biological activity than native extract Major Allergen Content Major allergen content (Der p 1 and Der p 2) is measured using the Indoor Biotech kits in *D. pteronyssinus*. Anti Der p 1 and or anti Der p 2 monoclonal IgG antibodies are coated (1:1000 from the vial prepared at 1 mg/ml for Der p 1 and 2 mg/ml for Der p 2) in polystyrene microtiter wells (NUNC Maxisorp). Standard curve is prepared using a quantified and standardized universal standard (sub-standardized against the WHO/IUIS *D. pteronyssinus* reference containing 2500 ng/ml of Der p 1 and 1000 ng/ml of Der p 2): The control curve dilutions are from 250-0.49 ng/ml for Der p 1 and 100-0.2 ng/ml for Der p 2. Mites samples are routinely diluted two-fold. After washing the plate, 100 µl of diluted allergen standard and samples are added and incubated for 1 hour at room temperature. After washing the plate, 100 µl of secondary antibody (monoclonal IgG antibody biotinilated) diluted 1/1000 are added and incubated for 1 hour at room temperature. After washing the plate, 100 µl of Streptavidin-Peroxidase diluted 1/1000 are added and incubate for 30 minutes at room temperature. Finally the plate is washed, developed adding 100 µl 1 mM ABTS in 70 mM citrate phosphate buffer, pH 4.2 containing a 1/1000 dilution of 30% H2O2 (i.e. 10 µl/10 ml ABTS) and read when the optical density at 405 nm reaches 2.0-2.4.

TABLE 6

Summary of results obtained for Example 5 (*Dermatophagoides pteronyssinus*)

| *Dermatophagoides pteronyssinus* | Yield (%) | ELISA inh. (IgE) µg 50% inh. | Lowry-Biuret µg prot./mg | UV-visible 1 mg/ml | Potency HEP-L/mg | µgDerp1/mg freeze-dried | µgDerp2/mg freeze-dried |
|---|---|---|---|---|---|---|---|
| Native | 4.59 | 0.161 | 251.7 | 1,909 (276 nm) | 327 | 8.49 | 7.98 |
| Depigmented pH2 | 34.7 | 0.268 | 238.1 | 1,851 (276 nm) | 339 | 0.37 | 14.62 |
| Depigmented pH2 | 63.7 | 0.136 | 257.8 | 2,057 (276 nm) | 555 | 8.96 | 12.18 |
| Depigmented pH2 | 67.6 | 0.110 | 271.4 | 2,188 (276 nm) | 873 | 13.32 | 10.92 |
| Depigmented pH2 | 79.1 | 0.127 | 265.5 | 2,122 (276 nm) | 1221 | 14.10 | 8.40 |
| Depigmented pH2 | 81.1 | 0.116 | 307.9 | 2,133 (276 nm) | 1705 | 13.20 | 8.55 |

Example 5—Mite Allergen Extract
(*Dermatophagoides pteronyssinus*)

Mite allergen extract was obtained following the method step B from full-grown culture of *Dermatophagoides pteronyssinus*.

The final product consists on a freeze-dried depigmented extract, to be stored at 4° C. in freeze-dried conditions. The resulting product has to meet the following specifications:
  a. Soluble product in water
  b. Similar protein profile than native extract, determined by SDS-PAGE and 2-D Example 6—Ragweed Allergen Extract
(*Phragmites communis*)

*Phragmites communis* pollen collected from the plant after pollination is defatted with cold acetone in a proportion 1:4 (w/v) under continuous stirring for 3 hours at 3-5° C. The resulting solution was filtered in a Buchner funnel and washed at least three times with fresh acetone. After finishing the process, the defatted extract was collected and dried at room temperature under a laminar flow hood for 12 hours, until the material was totally dry and all the acetone had been removed.

Depigmented polymerised *Phragmites* allergen extract was obtained in accordance with method steps B-D.

In step D the polymerization process consists of the addition of glutaraldehyde using a factor of 0.015 ml of glutaraldehyde/ml of extract.

The final product consists on a freeze-dried depigmented and polymerised *Phragmites* extract, to be stored at 4° C. in freeze-dried conditions. The resulting product has to meet the following specifications:
   a. Soluble product in water
   b. Absence of non-polymerised allergens/proteins with a molecular weight lower than 100 kDa (identified as bands by SDS-PAGE in non-reducing conditions)
   c. Absence of IgE recognition bands with a molecular weight lower than 100 kDa (identified by Immunoblot in non-reducing conditions)
   d. Absence of polymerised molecules in a molecular weight lower than 100 kDa (determined by size-exclusion chromatography with HPLC)
   e. Reduction of the free aminogroups (75%) respect to the native extract (determined by the fluram method)
   f. Significant reduction of the biological potency respect to the native extract (determined by IgE ELISA inhibition experiments using a specific pool of sera from sensitized individuals)
   g. Absence of abnormal toxicity in mice The pellet comprising depigmented/polymerised residue was utilised as a control in the characterisation of the native, depigmented and depigmented/polymerised extracts (refer to Table 7a and 7b).

TABLE 7a

Summary of results obtained for Example 6 (*Phragmites communis*)

| *Phragmites communis* | Yield (pellet) | ELISA inh.(IgE) 50% inhibition (μg) (% potency loss) | Protein content μg prot./mg | Fluram μg ACA/mg (% reduction amino group) | UV-visible 1 mg/ml Absorbance (nm) |
|---|---|---|---|---|---|
| Native | | 0.486 | 240.7 | 145 | 1.074 (272 nm) |
| Depigmented | | 0.847 | 321.5 | 103 | 0.844 (274 nm) |
| Depigmented-polymerised (0.009) | 80.7 (2.74) | 2.051 | 329.8 | 3.6 (95.7) | 1.891 (266 nm) |
| Depigmented-polymerised (0.0045). | 80.7 (3.1) | 1.217 | 381.4 | 6.3 (95.7) | 1.897 (268 nm) |
| Depigmented-polymerised (0.015) | 64.8 (4.75) | 5.080 | 306.2 | 1.6 (98.9) | 2.206 (268 nm) |
| Depigmented-polymerised (0.02) | 25.2 (2.5 | 5.035 | 306.1 | 24.3 (83.2) | 1.749 (266 nm) |

TABLE 7b

Summary of results obtained for Example 6 (*Phragmites communis*)

| *Phragmites communis* | SDS-PAGE (kDa) | Immunoblot (kDa) | Molecular size (kDa) |
|---|---|---|---|
| Native | 10-100 | 10-100 | 10-100 |
| Depigmented | 10-100 | 10-100 | 10-100 |
| Depigmented-polymerised (0.009) | >100 | Absent | >100 |
| Depigmented-polymerised (0.0045). | >100 | Absent | >100 |
| Depigmented-polymerised (0.015) | >100 | Absent | >100 |
| Depigmented-polymerised (0.02) | >100 | Absent | >100 |

Example 7 Cat Epithelia Allergen Extract

Cat hair is defatted with cold acetone in a proportion 1:40 (w/v) after five minutes stirring every hour for 7 hours at 3-5° C. The defatting continued for at least 16 hours without stirring. The resulting solution was filtered in a Buchner funnel and the flakes kept. The cat hair is again defatted with the same acetone for 1 hour at room temperature and repeated twice. The obtained flakes were collected and dried at room temperature under a laminar flow hood for 15 hours, until the material was totally dry and all the acetone had been removed.

In step B dried defatted skin flakes material obtained from cat hair is weighed and extracted in PBS 0.01 M/NaCl 0.15M in a proportion 1:40 for 4 hours at 3-5° C. and under magnetic stirring.

Depigmented polymerised cat allergen extract was obtained in accordance with method steps B-D.

The final product consists on a freeze-dried depigmented and polymerised cat epithelia extract, to be stored at 4° C. in freeze-dried conditions. The resulting product has to meet the following specifications:
   a. Soluble product in water
   b. Reduction of the free aminogroups (75%) respect to the native extract (determined by the fluram method)
   c. Significant reduction of the biological potency respect to the native extract (determined by IgE REINA competition experiments using a specific pool of sera from sensitized individuals)
   d. Detection of the major allergen Fel d 1. Monoclonal antibodies
   e. Absence of abnormal toxicity in mice Major Allergen Content Major allergen content Fel d 1 is measured using the Indoor Biotech kit. Anti Amb a 1 Monoclonal IgG1 antibody is coated (1:1000 from the vial prepared at 1 mg/ml). Standard curve is prepared using a Universal Allergen Standard which contains 1000 ng Fel d 1/ml. Secondary antibody consists on a Monoclonal antibody IgG1 biotinilated antibody raised against cat epithelia allergen. Native and Depigmented samples are diluted at 250 ng/ml. Major allergen content is calculated in polymerised extracts using these values.

The pellet comprising depigmented/polymerised residue was utilised as a control in the characterisation of the native, depigmented and depigmented/polymerised extracts, (refer to Table 8).

TABLE 8

Summary of results obtained for Example 7 (Cat epithelia)

| Cat epithelia | Yield (%) | ELISA inh. (IgE) 50% inhibition (μg) (% potency loss) | Protein content μg prot./mg | Fluram μg ACA/mg (% reduction amino group) | UV-visible 1 mg/ml Absorbance (nm) | Potency (HEPL/mg) | Fel d 1 μg/ml |
|---|---|---|---|---|---|---|---|
| Native | 10.3 | 0.029 | 154 | 14 | 0.396 (280 nm) | 1488 | 42 |
| Depigmented | 85.9 | 0.044 | 195 | 10.4 | 0.428 (280 nm) | 1478 | 42 |
| Depigmented-polymerised (0.009) | 96.2 | 0.192 | 171 | 1.5 (89%) | 0.701 (268 nm) | 28 | 8 |
| Depigmented-polymerised (0.013). | 92.9 | 0.373 | 183 | 1.3 (90.6%) | 0.698 (268 nm) | 23 | 7 |
| Depigmented-polymerised (0.02) | 90.6 | 0.494 | 169 | 1.2 (91.5%) | 0.769 (268 nm) | 17 | 2 |

Example 8 *Phleum pratense* Allergen Extract

*Phleum pratense* pollen collected from the plant after pollination was defatted with cold acetone in a proportion 1:4 (w/v) under continuous stirring for 3 hours at 3-5° C. The resulting solution was filtered in a Buchner funnel and washed at least three times with fresh acetone. After finishing the process, the defatted peanut extract was collected and dried at room temperature under a laminar flow hood for 12 hours, until the material was totally dry and all the acetone had been removed.

Depigmented polymerised *Phleum pratense* allergen extract was obtained in accordance with method steps B-D.

In step D the polymerization process consists on the addition of glutaraldehyde using a factor of 0.009 ml of glutaraldehyde/ml of extract.

The final product consists on a freeze-dried depigmented and polymerised *Phleum pratense* extract, to be stored at 4° C. in freeze-dried conditions. The resulting product has to meet the following specifications:

a. Soluble product in water
b. Absence of non-polymerised allergens/proteins with a molecular weight lower than 100 kDa (identified as bands by SDS-PAGE in non-reducing conditions)
c. Absence of IgE recognition bands with a molecular weight lower than 100 kDa (identified by Immunoblot in non-reducing conditions)
d. Absence of polymerised molecules in a molecular weight lower than 100 kDa (determined by size-exclusion chromatography with HPLC)
e. Reduction of the free aminogroups (75%) respect to the native extract (determined by the fluram method)
f. Significant reduction of the biological potency respect to the native extract (determined by IgE ELISA inhibition experiments using a specific pool of sera from sensitized individuals)
g. Absence of abnormal toxicity in mice Major Allergen Content Major allergen content Phl p 5 is measured using the Indoor Biotech kit. Anti Phl p 5 Monoclonal IgG1 antibody is coated (1:1000 from the vial prepared at 2 mg/ml). Standard curve is prepared using a recombinant Phl p 5a. Secondary antibody consists on a Monoclonal antibody IgG1 biotinilated antibody raise against *Phleum pratense* allergen. Native and Depigmented samples are diluted at 250 ng/ml. Major allergen content is calculated in polymerised extracts using these values.

The pellet comprising depigmented/polymerised residue was utilised as a control in the characterisation of the native, depigmented and depigmented/polymerised extracts (refer to Table 9).

TABLE 9

Summary of results obtained for Example 8 (*Phleum pratense*)

| *Phleum pratense* | Yield (%) | ELISA inh. (IgE) 50% inhibition (μg) (% potency loss) | Protein content μg prot./mg | Potency (HEPL/mg) | SDS-PAGE kDa | Immunoblot | Molecular size. kDa |
|---|---|---|---|---|---|---|---|
| Native | 8.42 | 0.089 | 409.9 | 904.5 | 10-100 | 1478 | 10-100 |
| Depigmented-polymerised (0.009) | 45.0 | 00.341 | 446.0 | 35.3 | 10-100 | 28 | 10-100 |
| Depigmented-polymerised (0.009) | 98.0 | 0.305 | 464.3 | 13.2 | >100 | Absent | >100 |

TABLE 9-continued

Summary of results obtained for Example 8 (*Phleum pratense*)

| Phleum pratense | Yield (%) | ELISA inh. (IgE) 50% inhibition (μg) (% potency loss) | Protein content μg prot./mg | Potency (HEPL/mg) | SDS-PAGE kDa | Immunoblot | Molecular size. kDa |
|---|---|---|---|---|---|---|---|
| Depigmented-polymerised (0.013). | 19.85 | 0.429 | 420.5 | 19.3 | >100 | Absent | >100 |
| Depigmented-polymerised (0.02) | 57.5 | 1.274 | 1234.8 | 14.4 | >100 | Absent | >100 |

LITERATURE REFERENCES

1. Vickery, B., Burks, W. *Immunotherapy in the treatment of food allergy: focus oral tolerance*. Curr. Opin. Allergy Clin. Immunol. 2009; 9:364-370.
2. King, R. M., Knibb, R. C., and Hourihane, J. O. B. *Impact of peanut allergy on quality of life, stress and anxiety in the family*. Allergy 2009; 64: 461-468.
3. Enrique, E., Pineda, F., Malek, T., Bartra, J., Basagaña, M., Tella, R., Castelló, J. V., Alonso, R., de Mateo, J. A., Cerdá-Trias, T., San Miguel-Moncín Mdel, M., Monzón, S., García, M., Palacios, R., Cisteró-Bahíma, A. *Sublingual immunotherapy for hazelnut food allergy: a randomized, double-blind, placebo-controlled study with a standardized hazelnut extract*. J. Allergy Clin. Immunol. 2005; 116(5):1073-9.
4. Fernández-Rivas, M., Garrido Fernández, S., Nadal, J. A., Díaz de Durana, M. D., García, B. E., González-Mancebo, E., Martín, S., Barber, D., Rico, P., Tabar, A. I. *Randomized double-blind, placebo-controlled trial of sublingual immunotherapy with a Pru p 3 quantified peach extract*. Allergy. 2009; 64(6):876-83.
5. Hofmann, A. M., Scurlock, A. M., Jones, S. M., Palmer, K. P., Lokhnygina, Y., Steele, P. H., Kamilaris, J., Burks, A. W. *Safety of a peanut oral immunotherapy protocol in children with peanut allergy*. J. Allergy Clin. Immunol. 2009 May 26.
6. Jones, S. M., Pons, L., Roberts, J. L., Scurlock, A. M., Perry, T. T., Kulis, M., Shreffler, W. G., Steele, P., Henry, K. A., Adair, M., Francis, J. M., Durham, S., Vickery, B. P., Zhong, X., Burks, A. W. *Clinical efficacy and immune regulation with peanut oral immunotherapy*. J. Allergy. Clin. Immunol. 2009 August; 124(2):292-300, 300.
7. Clark, A. T., Islam, S., King, Y. *Successful oral tolerance induction in severe peanut allergy*. Allergy 2009 August; 64(8):1218-20.
8. Wallace D V. *Pet dander and perennial allergic rhinitis: therapeutic options*. Allergy Asthma Proc. 2009 November-December; 30(6):573-83.
9. Ling M, Long A A *Pet dander and difficult-to-control asthma: Therapeutic options*. Allergy Asthma Proc. 2010 September; 31(5):385-91.
10. Grönlund H, Saarne T, Gafvelin G, van Hage M. *The major cat allergen, Fel d 1, in diagnosis and therapy*. Int Arch Allergy Immunol. 2010; 151(4):265-74. Epub 2009 Oct. 22. Review.

WEBSITE REFERENCES

[1]. Allergen nomenclature. International Union of Immunological Societies Allergen Nomenclature Sub-Committee. List last update 21 Jul. 2009.

TABLE 2

Effects of glutaraldehyde final concentration and addition rate on polymerisation

| | Peanut | Batch | Glutaraldehyde Final concentration factor (addition rate) | polymer yield % | residue yield % | Total yield % | SDS-PAGE Bands < 100 kDa reducing conditions | | SDS-PAGE Bands < 100 kDa nonreducing conditions | | WESTERN-BLOT Bands < 100 kDa reducing conditions | | WESTERN-BLOT Bands < 100 kDa nonreducing conditions | |
|---|---|---|---|---|---|---|---|---|---|---|---|---|---|---|
| | | | | | | | polymer | residue | polymer | residue | polymer | residue | polymer | residue |
| Tests to establish the appropriate glutaraldehyde concentration and addition rate | Depigoid | 250808/LP | 4.5 mg/ml 0.009 (manual) | 45 | 12.96 | 57.96 | yes | | yes | | yes | | yes | |
| | Depigoid | 260808/LP | 15 mg/ml 0.03 (manual) | 7 | 5.85 | 12.85 | yes | | yes | | yes | | yes | |
| | Depigoid | 270808/LP | 50 mg/ml 0.1 (manual) | 8.6 | 49.85 | 58.45 | yes | | yes | | yes | | yes | |
| | Depigoid | 020908/LP | 4.5 mg/ml 0.009 (100 μl/min) | 41.8 | 11.4 | 53.2 | yes | | yes | | yes | | yes | |
| | Depigoid | 030908/LP | 4.5 mg/ml 0.009 | 41.3 | 24.3 | 65.6 | yes | | yes | | yes | | yes | |

TABLE 2-continued

Effects of glutaraldehyde final concentration and addition rate on polymerisation

| | | | | | | | SDS-PAGE | | | | WESTERN-BLOT | | | |
|---|---|---|---|---|---|---|---|---|---|---|---|---|---|---|
| | | | Glutar-aldehyde Final concentration | poly-mer | res-idue | Total | Bands < 100 kDa reducing conditions | | Bands < 100 kDa nonreducing conditions | | Bands < 100 kDa reducing conditions | | Bands < 100 kDa nonreducing conditions | |
| | Peanut | Batch | factor (addition rate) | yield % | yield % | yield % | poly-mer | res-idue | poly-mer | res-idue | poly-mer | res-idue | poly-mer | res-idue |
| | Depigoid | 040908/LP | (10 μl/min) 4.5 mg/ml 0.009 | 33.8 | 28.6 | 62.4 | yes | yes | yes | yes | | | | |
| | Depigoid | 230908/LP | (3 μl/min) 10 mg/ml 0.02 | 14.3 | 41.13 | 55.43 | yes | yes | no | yes | | | | |
| | Depigoid | 240908/LP | (133 μl/min) 10 mg/ml 0.02 | 12.83 | 42.15 | 54.98 | yes | yes | no | yes | | | | |
| | Depigoid | 250908/LP | (20 μl/min) 10 mg/ml 0.02 | * | 44 | * | * | yes | * | yes | | | | |
| | Depigoid | 300908/LP | (6.6 μl/min) 2.25 mg/ml 0.0045 | 52.65 | 12 | 64.65 | yes | yes | yes | yes | | | | |
| Proyect peanut (fried/ | Depigoid | 030309/LP | (100 μl/min) 10 mg/ml 0.02 | 9.1 | 46.3 | 55.4 | yes | yes | no | yes | yes | yes | no | no |
| raw) | Depigoid | 030309/LP | (100 μl/min) 10 mg/ml 0.02 | 9.1 | 46.3 | 55.4 | yes | yes | no | yes | yes | yes | no | no |

* polymer was lost

The invention claimed is:

1. A process for producing an allergen extract comprising:
   a) contacting a source material comprising allergen with acetone to produce a mixture containing lipids dissolved in liquid phase and a solid phase consisting of source material residue comprising allergens and proteins,
   b) subjecting the mixture to a first separation step to isolate the source material residue,
   c) contacting the source material residue with an aqueous solution to produce a mixture of allergens dissolved in liquid phase, and a solid phase consisting of non-allergenic residue,
   d) subjecting the mixture to a second separation step to isolate the allergens dissolved in liquid phase, to produce a crude allergen extract,
   e) subjecting the crude allergen extract to a first low molecular fraction removal step to remove molecules having a molecular size of less than 3.5 kDa,
   f) carrying out step e) until the crude allergen extract has conductivity of below 1000 μS/cm at 3-5° C. to obtain a purified native allergen extract, and
   g) acidifying the purified native allergen extract to pH 2 to 4 to produce an acidified purified native allergen extract and maintaining the acidified purified native allergen extract for 5-30 minutes, followed by subjecting the acidified purified native allergen extract to a second low molecular fraction removal step to remove molecules having a molecular size of less than 3.5 kDa, and adjusting the pH to 7.0-8.0 to produce a depigmented allergen extract.

2. The process as claimed in claim 1 wherein step (f) comprises carrying out step e) until the crude allergen extract has conductivity of less than 500 μS/cm at 3-5° C.

3. The process as claimed in claim 1 wherein the purified native allergen extract is acidified to pH 2 to 2.1.

4. The process as claimed in claim 1 wherein the purified native allergen extract is acidified to pH 2.0 to 3.0.

5. The process as claimed in claim 1, further comprising a polymerization step, comprising:
   h) contacting the depigmented allergen extract with glutaraldehyde or formaldehyde to produce a crude depigmented polymerized allergen extract,
   i) subjecting the crude depigmented polymerized allergen extract to a molecular fraction removal step to remove molecules having a molecular size of less than 100 kDa, and
   j) carrying out step i) until the crude depigmented polymerized allergen extract has a conductivity of below 210 μS/cm at 3-5° C. and/or is absent of glutaraldehyde as determined by UV or visible scanning, to obtain a purified depigmented polymerized allergen extract.

6. The process as claimed in claim 1, wherein the source material is selected from the group consisting of food allergens, peanuts, whole peanuts, air-borne allergens, dust mites, fungi, molds, mites, grasses, tree and weed allergens, epithelial allergens, and insect allergens.

7. The process as claimed in claim 5, wherein the purified depigmented polymerized allergen extract is used in the treatment of an allergy.

8. A process according to claim 5, wherein step (j) comprises carrying out step i) until the crude depigmented polymerized allergen extract has a conductivity between 50 and 200 μS/cm at 3-5° C.

9. A process according to claim 1, wherein at least one of the first low molecular fraction removal step in step e) or the second low molecular fraction removal step in step g) comprises an ultrafiltration step, a diafiltration step, a dialysis step or filtration.

10. A process according to claim 6, wherein the air-borne allergens are pollen, the epithelial allergens are animal hair or animal dander, and the insect allergens are allergens from cockroaches, fleas, bees or wasp venom.

11. A process according to claim 1, wherein the source material is selected from the group consisting of food allergens, pollen, fungi and molds, epithelial allergens, and insect allergens.

12. A process according to claim 11, wherein the food allergens are allergens from *Arachis hypogaea*, the pollen is from *Alnus glutinosa, Betula alba, Corylus avellana, Cupressus arizonica, Olea europea, Platanus* sp, *Cynodon dactylon, Dactylis glomerata, Festuca elatior, Holcus lanatus, Lolium perenne, Phleum pratense, Phragmites communis, Poa pratensis, Ambrosia elatior, Artemisia vulgaris, Chenopodium album, Parietaria judaica, Plantago lanceolata, Salsola kali, Avena sativa, Hordeum vulgare, Secale cereal, Triticum aestivum, Zea mays)*, dust mites (*Acarus siro, Blomia tropicalis, Dermatophagoides farinae, Dermatophagoides microceras, Dermatophagoides pteronyssinus, Euroglyphus maynei, Lepidoglyphus destructor, Tyrophagus putrescentiae*, the fungi and molds are *Alternaria alternate, Cladosporium herbarum*, or *Aspergillus fumigatus*, the epithelias allergens are cat hair, cat dander, dog hair, dog dander, horse hair, horse dander, human hair, human dander, rabbit hair, rabbit dander, or feathers, and the insect allergens are from ants, fleas, mites, cockroaches, wasp venom, or bee venom.

13. A process according to claim 1, wherein the source material is selected from the group consisting of *Arachis hypogaea, Olea europaea* pollen, *Parietaria judaica* pollen, *Phragmites communis* pollen, *Phleum pratense* pollen, *Dermatophagoides pteronyssinus*, and cat dander.

14. A process according to claim 1, wherein the source material is *Arachis hypogaea*.

* * * * *